(12) United States Patent
Klinkenberg

(10) Patent No.: US 11,833,307 B2
(45) Date of Patent: Dec. 5, 2023

(54) CONNECTOR ASSEMBLY FOR A PATIENT INTERFACE

(71) Applicant: ResMed Pty Ltd, Bella Vista (AU)

(72) Inventor: Luke Emmanuel Klinkenberg, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 616 days.

(21) Appl. No.: 16/966,690

(22) PCT Filed: Feb. 1, 2019

(86) PCT No.: PCT/AU2019/050072
§ 371 (c)(1),
(2) Date: Jul. 31, 2020

(87) PCT Pub. No.: WO2019/148243
PCT Pub. Date: Aug. 8, 2019

(65) Prior Publication Data
US 2021/0030990 A1 Feb. 4, 2021

Related U.S. Application Data

(60) Provisional application No. 62/625,571, filed on Feb. 2, 2018.

(51) Int. Cl.
*A61M 16/08* (2006.01)
*A61M 16/06* (2006.01)
*A61M 16/00* (2006.01)

(52) U.S. Cl.
CPC .... *A61M 16/0816* (2013.01); *A61M 16/0057* (2013.01); *A61M 16/0633* (2014.02);
(Continued)

(58) Field of Classification Search
CPC .............. A61M 16/06; A61M 16/0616; A61M 16/0683; A61M 16/08; A61M 16/0816;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

CN 101951984 A 1/2011
CN 102458547 A 5/2012
(Continued)

OTHER PUBLICATIONS

Merriam-Webster, Definition for "snug fit", searched on Jan. 24, 2023 and saved to PDF. (Year: 2023).*
(Continued)

*Primary Examiner* — Kendra D Carter
*Assistant Examiner* — Allison S. Lown
(74) *Attorney, Agent, or Firm* — Nixon & Vanderhye P.C.

(57) ABSTRACT

A patient interface to deliver of a flow of air at a positive pressure with respect to ambient air pressure to an entrance to the patient's airways including at least the entrance of a patient's nares while the patient is sleeping, to ameliorate sleep disordered breathing, includes a seal-forming structure, a positioning and stabilising structure, and a connector assembly adapted to connect to an air circuit. The connector assembly includes a ring member configured to be removably and releasably secured in the patient interface and an elbow assembly configured to connect to the air circuit. The elbow assembly is repeatedly connectable to and disconnectable from the ring member. The elbow assembly includes an elbow member and a clip member that includes a separate and distinct structure from the elbow member, and the clip member is configured and arranged to connect to the elbow member.

21 Claims, 45 Drawing Sheets

(52) U.S. Cl.
CPC ..... *A61M 16/0683* (2013.01); *A61M 16/0616* (2014.02); *A61M 2202/0208* (2013.01); *A61M 2210/0618* (2013.01)

(58) Field of Classification Search
CPC .................. A61M 39/00; A61M 39/10; A61M 2039/1077; A62B 18/02
See application file for complete search history.

(56) References Cited

U.S. PATENT DOCUMENTS

| | | | |
|---|---|---|---|
| 6,491,034 B1* | 12/2002 | Gunaratnam | A61M 16/0683 128/912 |
| 6,532,959 B1 | 3/2003 | Berthon-Jones | |
| 6,581,594 B1 | 6/2003 | Drew et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 11,389,612 B2* | 7/2022 | O'Connor | A61M 16/06 |
| 2003/0196658 A1* | 10/2003 | Ging | A61M 16/0666 128/201.22 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2012/0138061 A1* | 6/2012 | Dravitzki | A61M 16/0825 128/205.25 |
| 2012/0222680 A1 | 9/2012 | Eves et al. | |
| 2016/0325067 A1 | 11/2016 | Harwood et al. | |
| 2017/0232219 A1 | 8/2017 | Dravitzki et al. | |

FOREIGN PATENT DOCUMENTS

| | | | |
|---|---|---|---|
| CN | 105120935 A | 12/2015 | |
| JP | 2000-279520 A | 10/2000 | |
| JP | 2017-108902 A | 6/2017 | |
| WO | WO 98/004310 A1 | 2/1998 | |
| WO | WO 98/034665 A1 | 8/1998 | |
| WO | WO 2000/078381 A1 | 12/2000 | |
| WO | WO 03/090827 A1 | 11/2003 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/135785 A1 | 12/2010 | |
| WO | WO 2012/171072 A1 | 12/2012 | |
| WO | WO 2013/020167 A1 | 2/2013 | |
| WO | WO 2015/088362 A1 | 6/2015 | |
| WO | WO-2015088362 A1 * | 6/2015 | ............ A61M 16/06 |
| WO | WO 2017/049356 A1 | 3/2017 | |
| WO | WO 2017/049357 A1 | 3/2017 | |
| WO | WO 2017/049358 A1 | 3/2017 | |
| WO | WO 2017/124152 A1 | 7/2017 | |
| WO | WO 2017/124155 A1 | 7/2017 | |

OTHER PUBLICATIONS

Notification of the First Office Action dated Oct. 10, 2022 in Chinese Application No. 201980015159.1, with English translation, 18 pages.
"*Respiratory Physiology*", by John B. West, Lippincott Williams & Wilkins, 9th edition published 2012, 8 pages.
International Search Report dated Apr. 16, 2019 in International Application No. PCT/AU2019/050072, 8 pages.
Written Opinion of the International Searching Authority dated Apr. 16, 2019 in International Application No. PCT/AU2019/050072, 7 pages.
International Preliminary Report on Patentability and Written Opinion of the International Searching Authority dated Aug. 4, 2020 in International Application No. PCT/AU2019/050072, 8 pages.

* cited by examiner

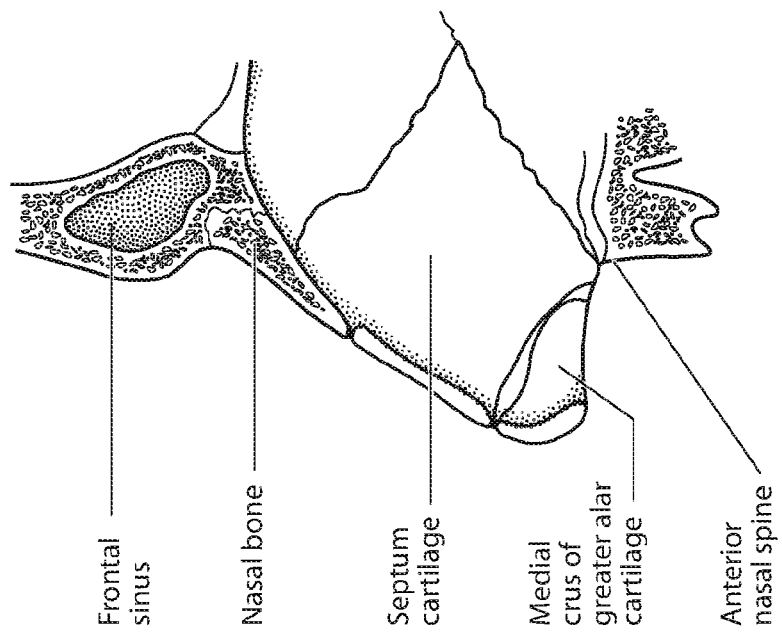
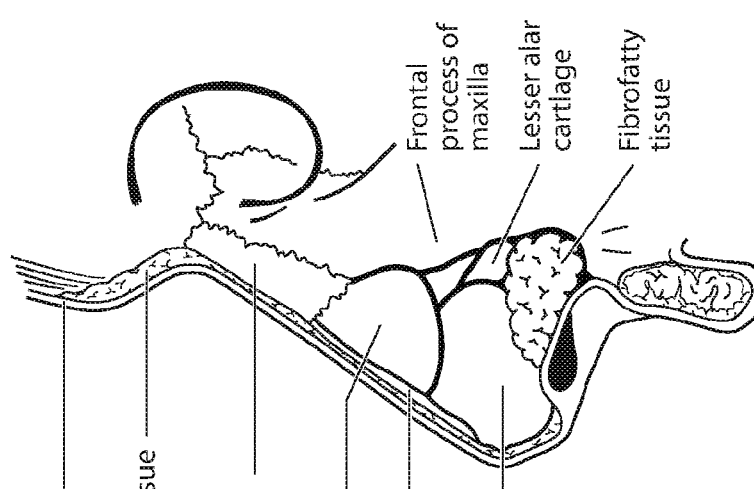
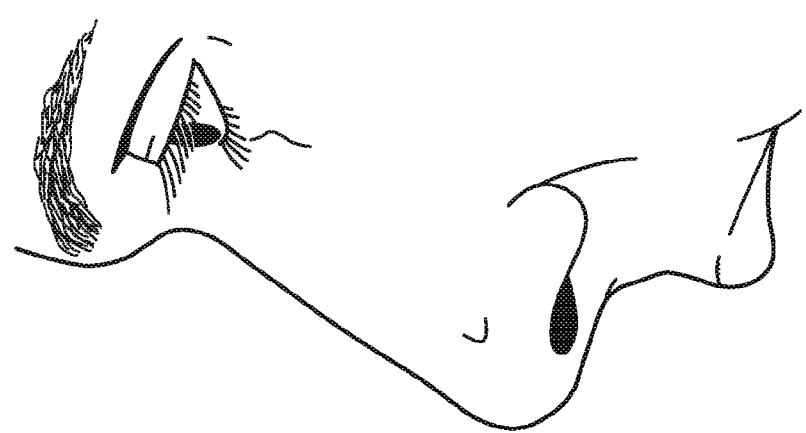
FIG. 2I
FIG. 2H
FIG. 2G

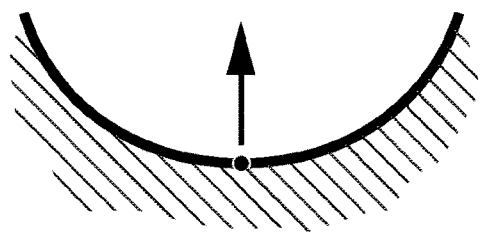
FIG. 3B  Relatively Large Positive Curvature
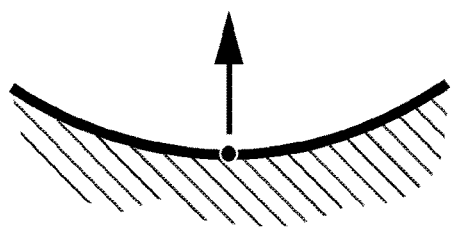
FIG. 3C  Relatively Small Positive Curvature
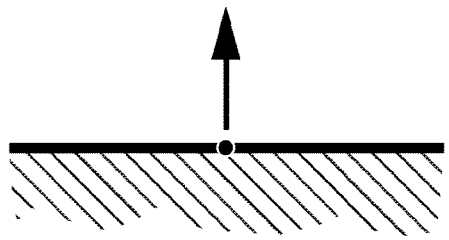
FIG. 3D  Zero Curvature
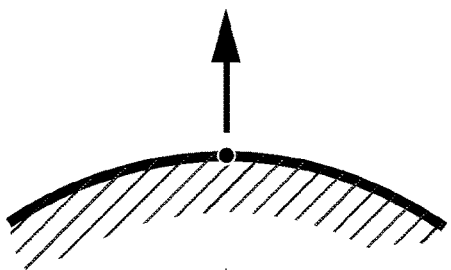
FIG. 3E  Relatively Small Negative Curvature
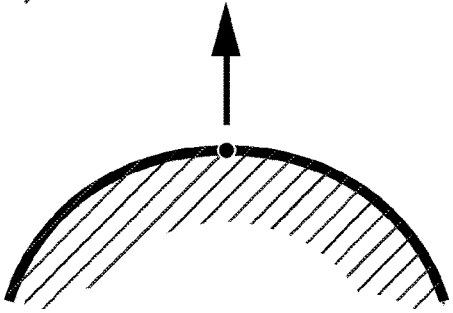
FIG. 3F  Relatively Large Negative Curvature
Copyright 2015 ResMed Limited

Left-hand rule

Right-hand rule

Left ear helix

Right-hand helix
Right-hand positive

Right ear helix

CONNECTOR ASSEMBLY FOR A PATIENT INTERFACE

1 CROSS-REFERENCE TO RELATED APPLICATIONS

This application is the U.S. national phase of International Application No. PCT/AU2019/050072 filed Feb. 1, 2019 which designated the U.S. and claims priority to U.S. Provisional Patent Application No. 62/625,571 filed Feb. 2, 2018, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NW) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact on the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to implement one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology relates to a connector assembly for a patient interface comprising separately molded parts to allow fewer restraints on materials.

An aspect of the present technology relates to a connector assembly for a patient interface comprising low profile button portions.

An aspect of the present technology relates to a patient interface to deliver of a flow of air at a positive pressure with respect to ambient air pressure to an entrance to the patient's airways including at least the entrance of a patient's nares while the patient is sleeping, to ameliorate sleep disordered breathing. The patient interface includes a seal-forming structure constructed and arranged to form a seal with a region of a patient's face surrounding the entrance to the patient's airways, a positioning and stabilising structure to provide a force to hold the seal-forming structure in a therapeutically effective position on a patient's head, and a connector assembly adapted to connect to an air circuit. The connector assembly includes a ring member configured to be removably and releasably secured in an aperture of an attachment region of the patient interface and an elbow assembly configured to connect to the air circuit. The elbow assembly is repeatedly connectable to and disconnectable from the ring member. The elbow assembly includes an elbow member and a clip member. The clip member includes a separate and distinct structure from the elbow member, and the clip member is structured and arranged to connect to the elbow member. The clip member is configured and arranged to releasably connect the elbow assembly to the ring member, and the elbow member is configured and arranged to form a seal with the ring member when the elbow assembly and the ring member are connected to one another.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
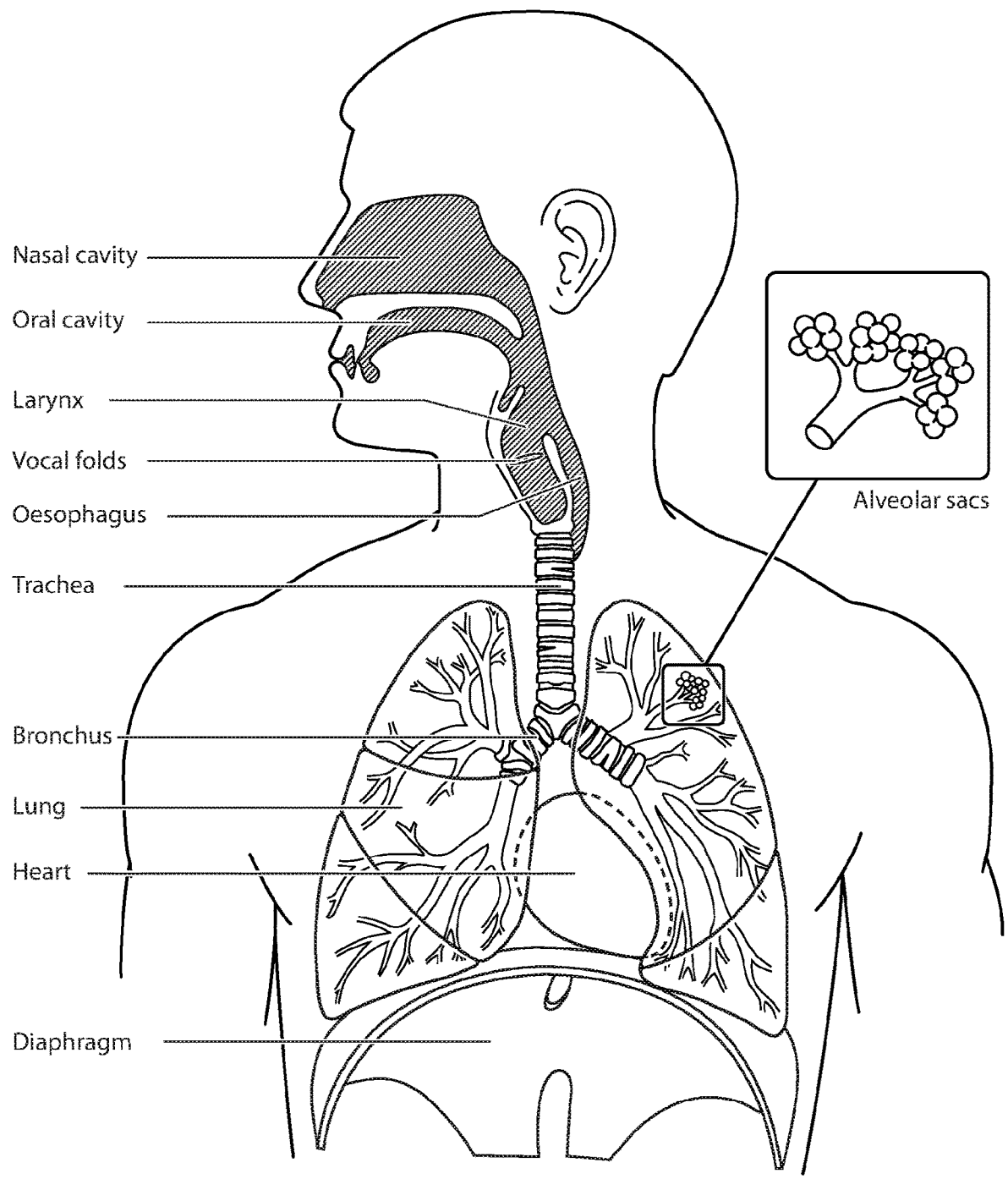
FIG. 2A shows an overview of a human respiratory system including the nasal and oral cavities, the larynx, vocal folds, oesophagus, trachea, bronchus, lung, alveolar sacs, heart and diaphragm.
Figure 2B:
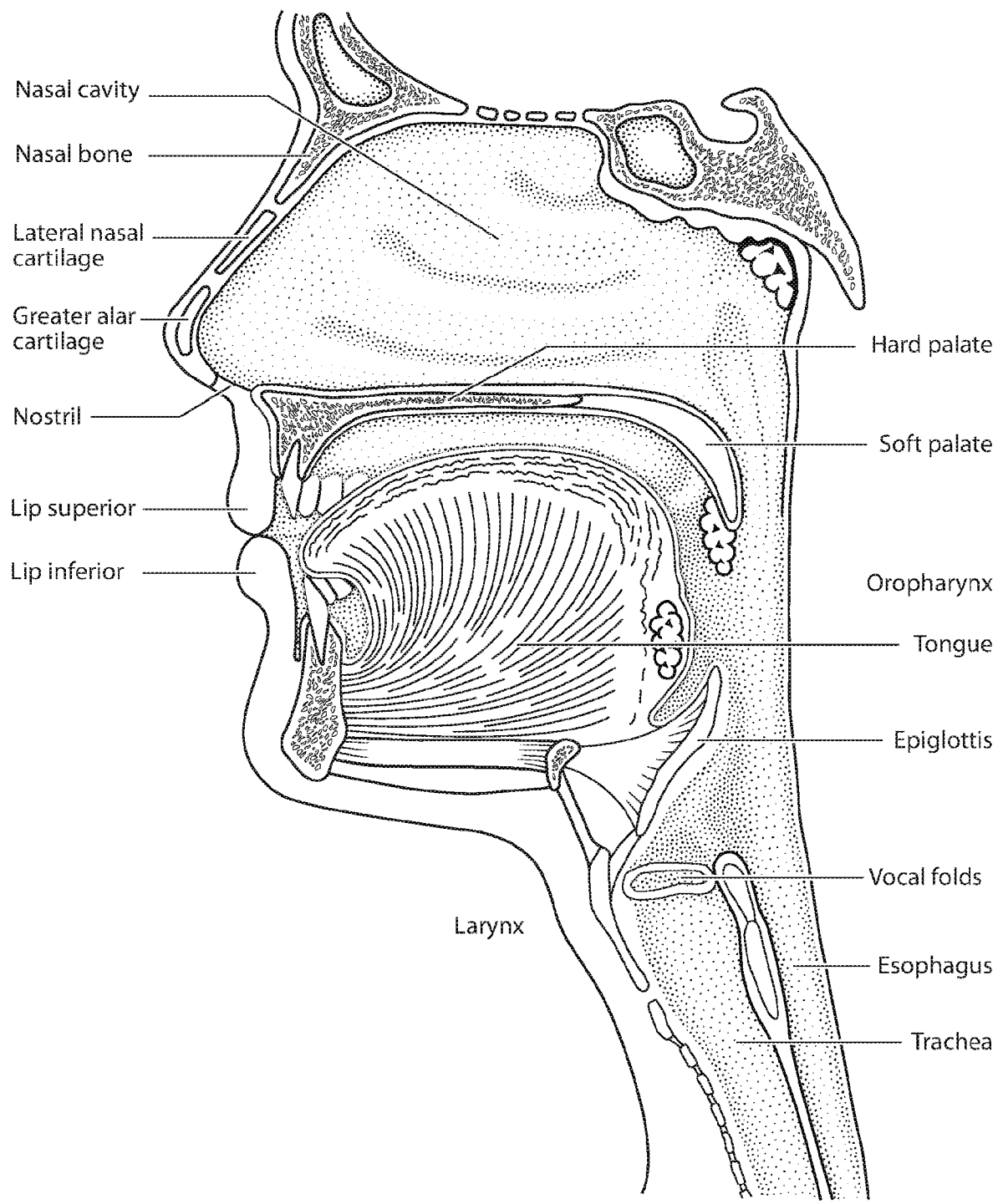
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
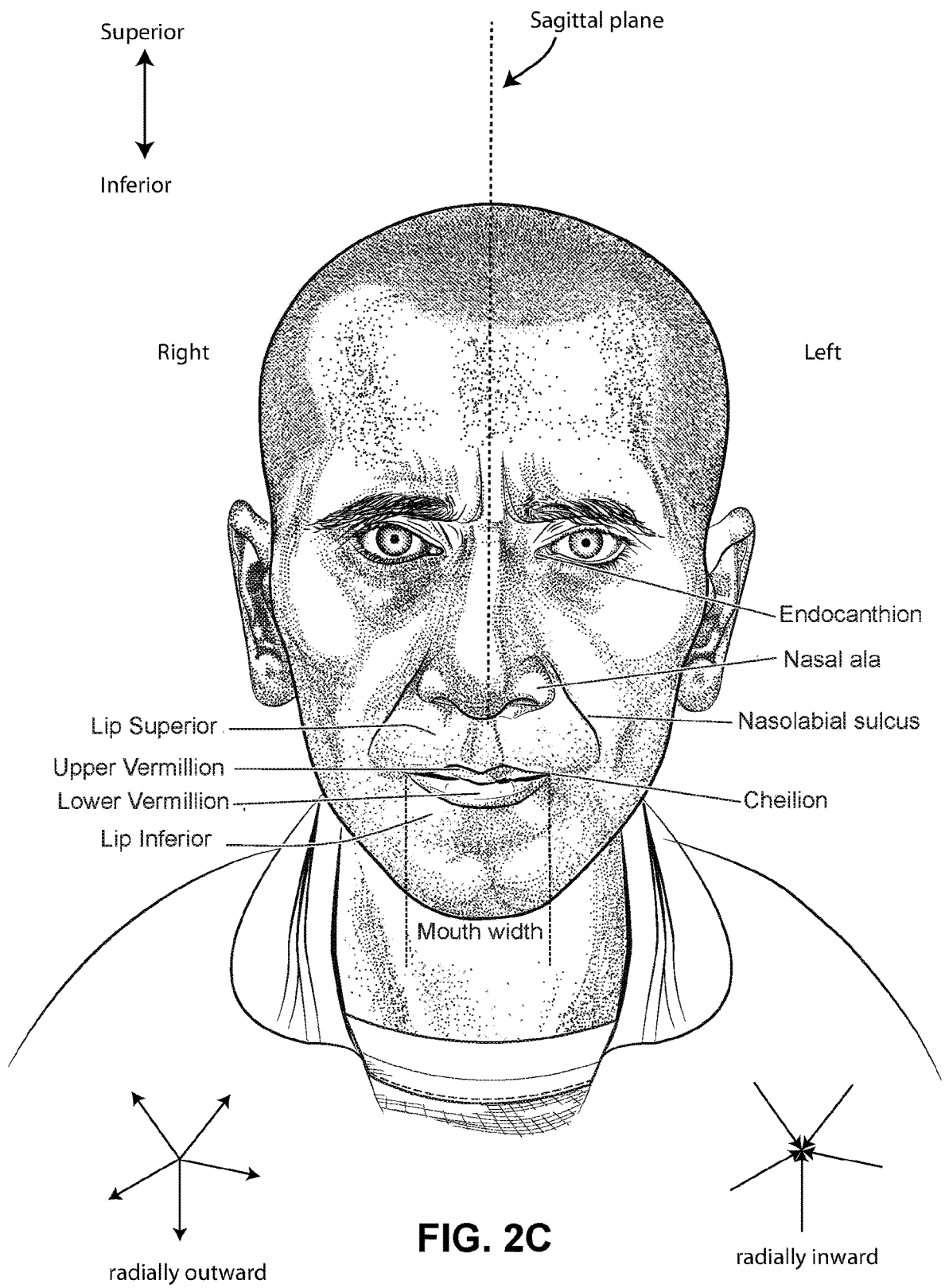
FIG. 2C is a front view of a face with several features of surface anatomy identified including the lip superior, upper vermilion, lower vermilion, lip inferior, mouth width, endo-canthion, a nasal ala, nasolabial sulcus and cheilion. Also indicated are the directions superior, inferior, radially inward and radially outward.
Figure 2D:
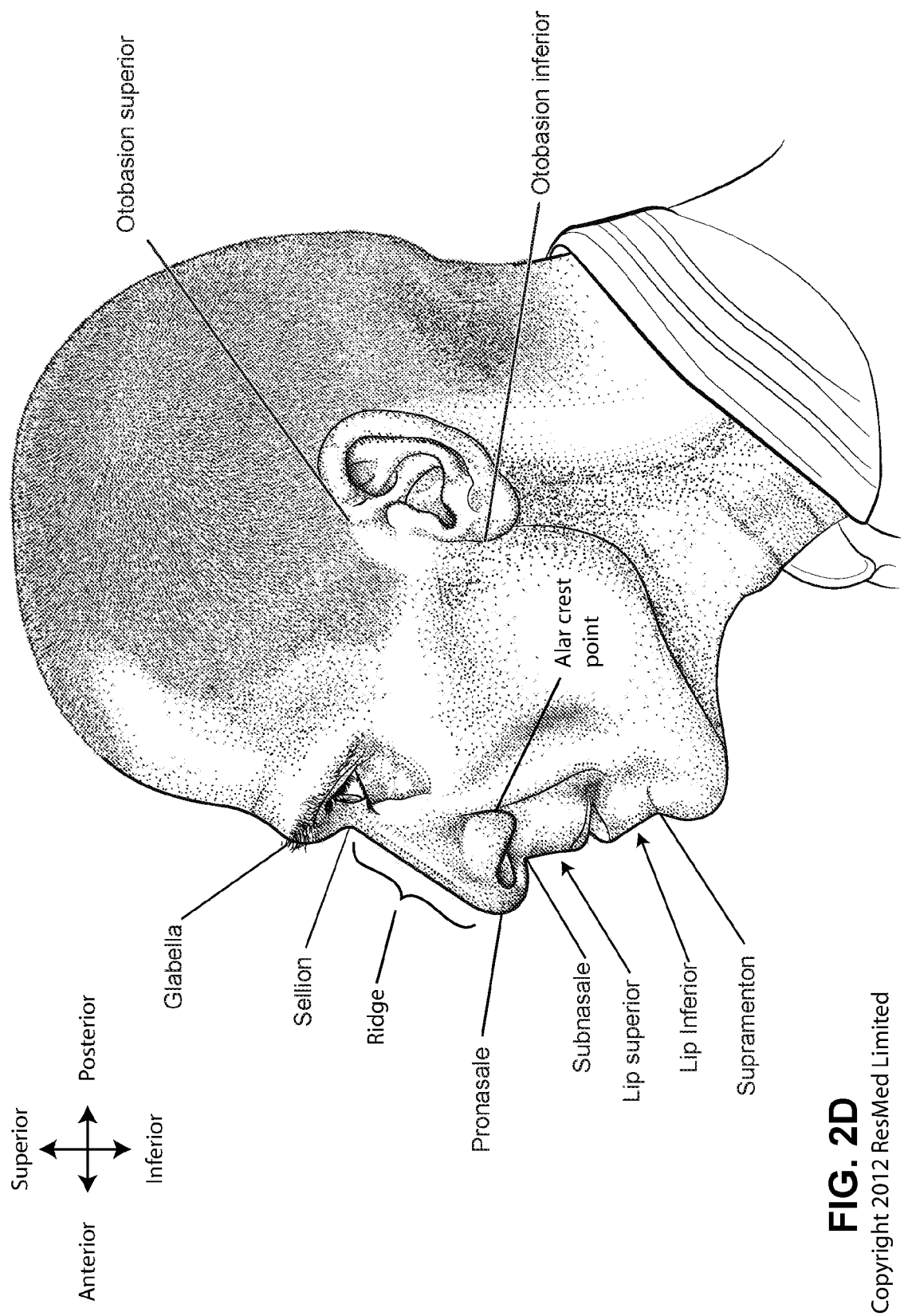
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
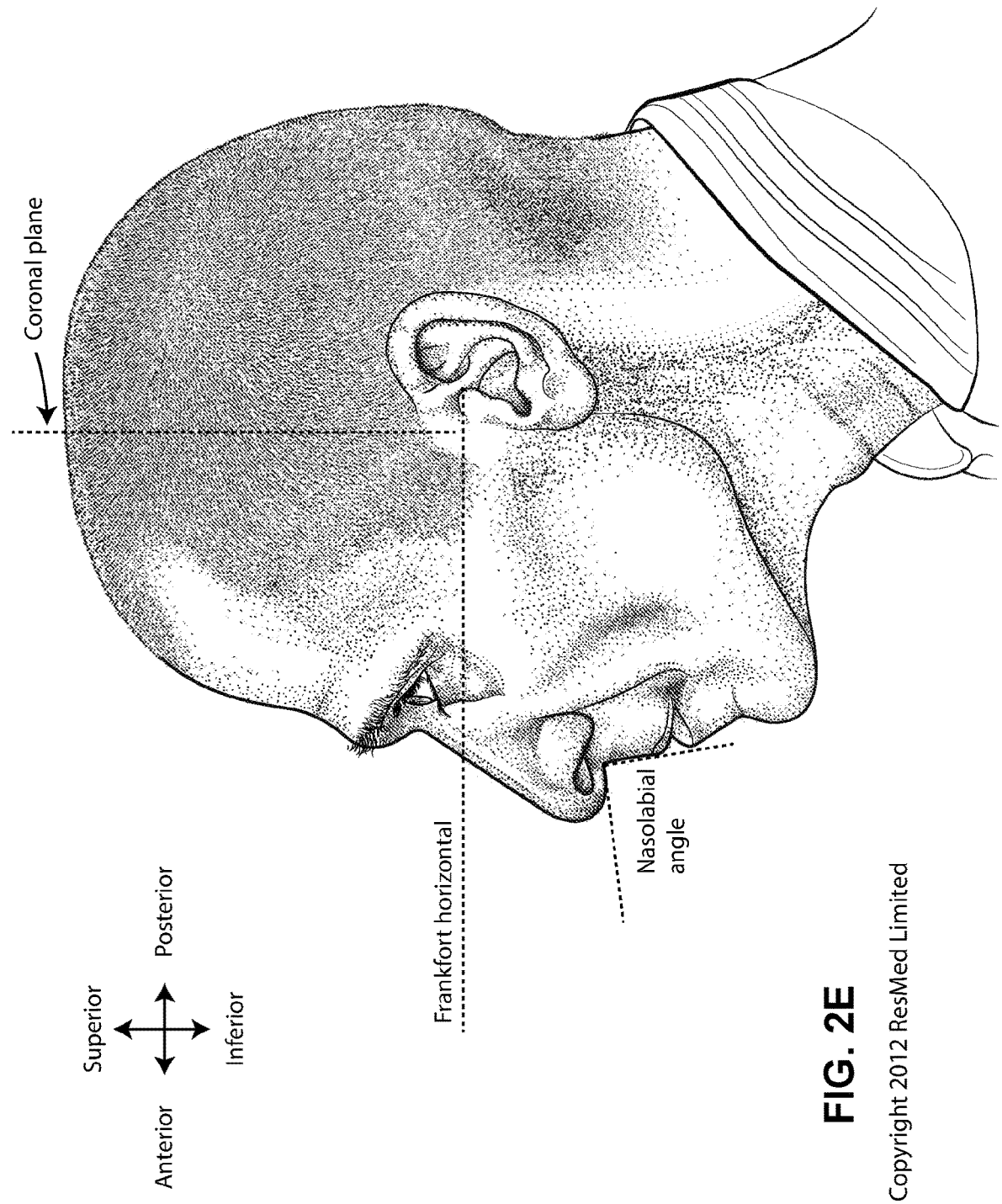

FIG. 2E is a further side view of a head. The approximate locations of the Frankfort horizontal and nasolabial angle are indicated. The coronal plane is also indicated.

Figure 2F:
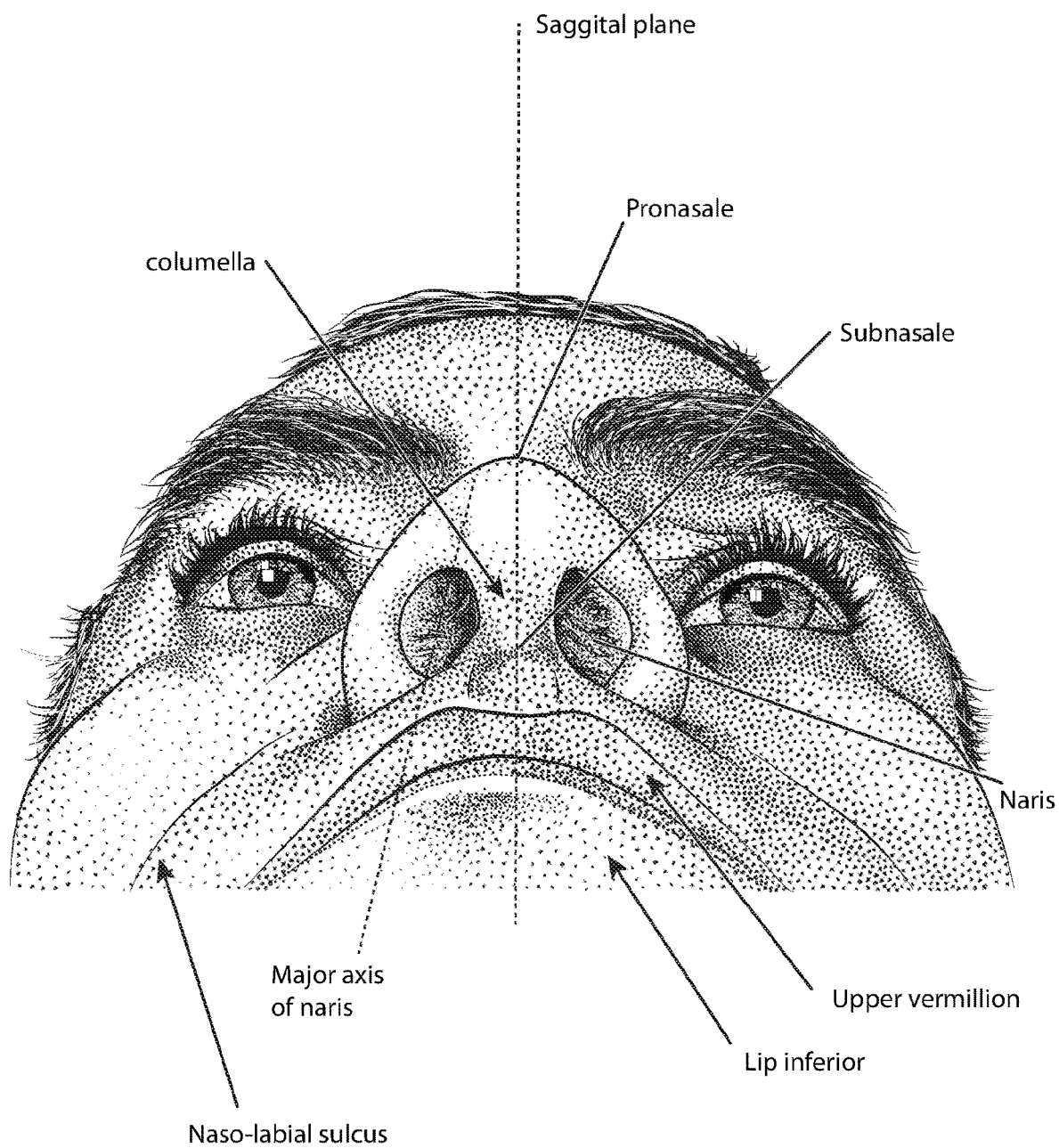

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
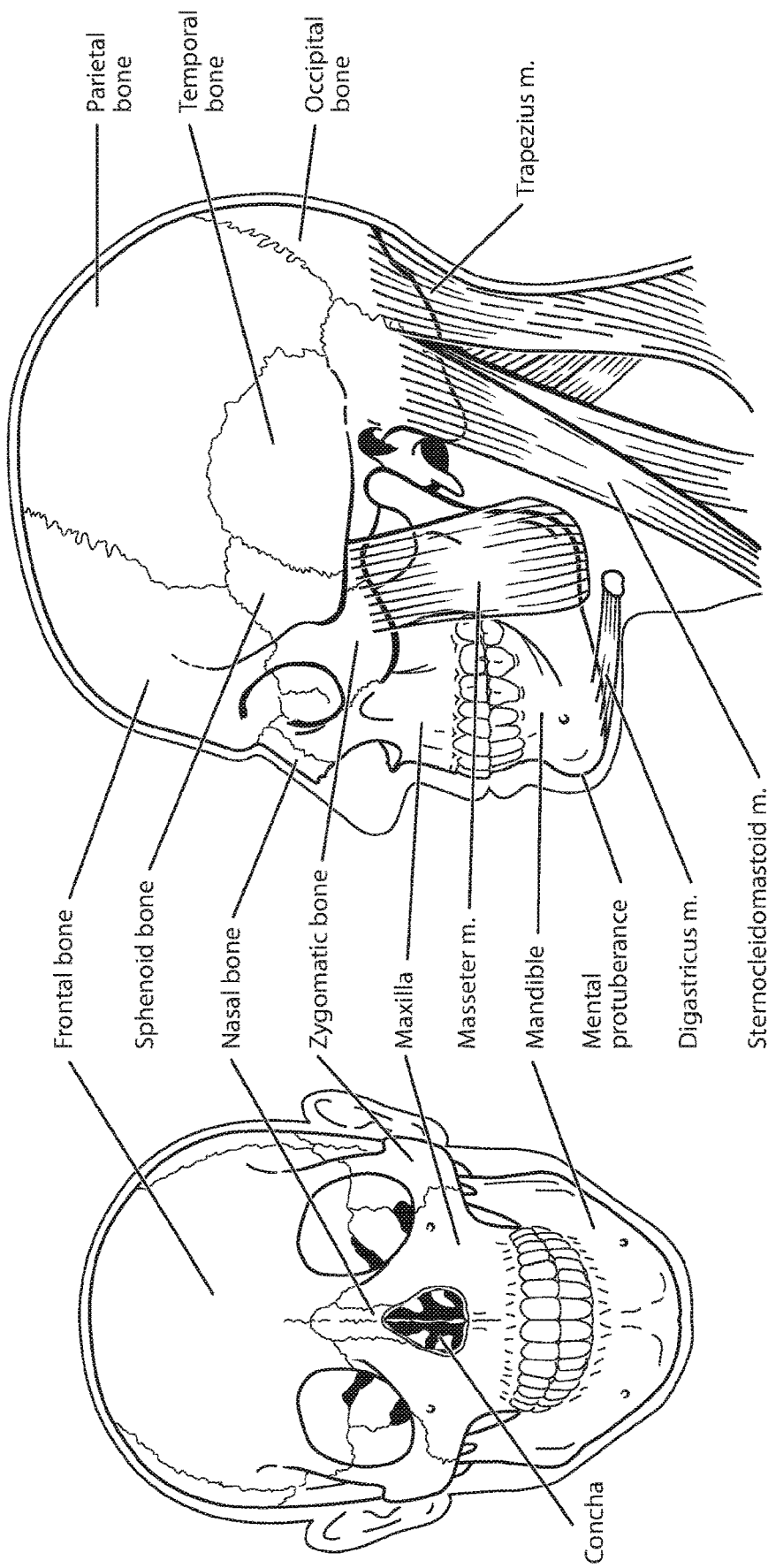

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
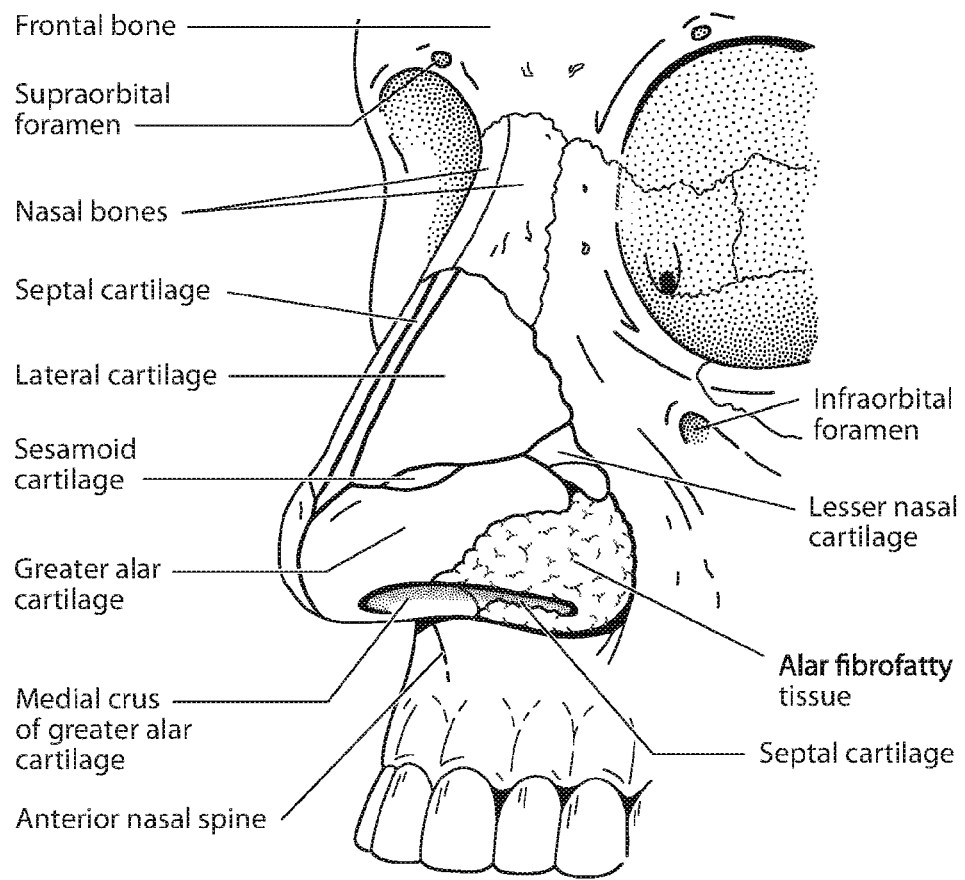

FIG. 2L shows an anterolateral view of a nose.

4.3 Patient Interface

Figure 3A:
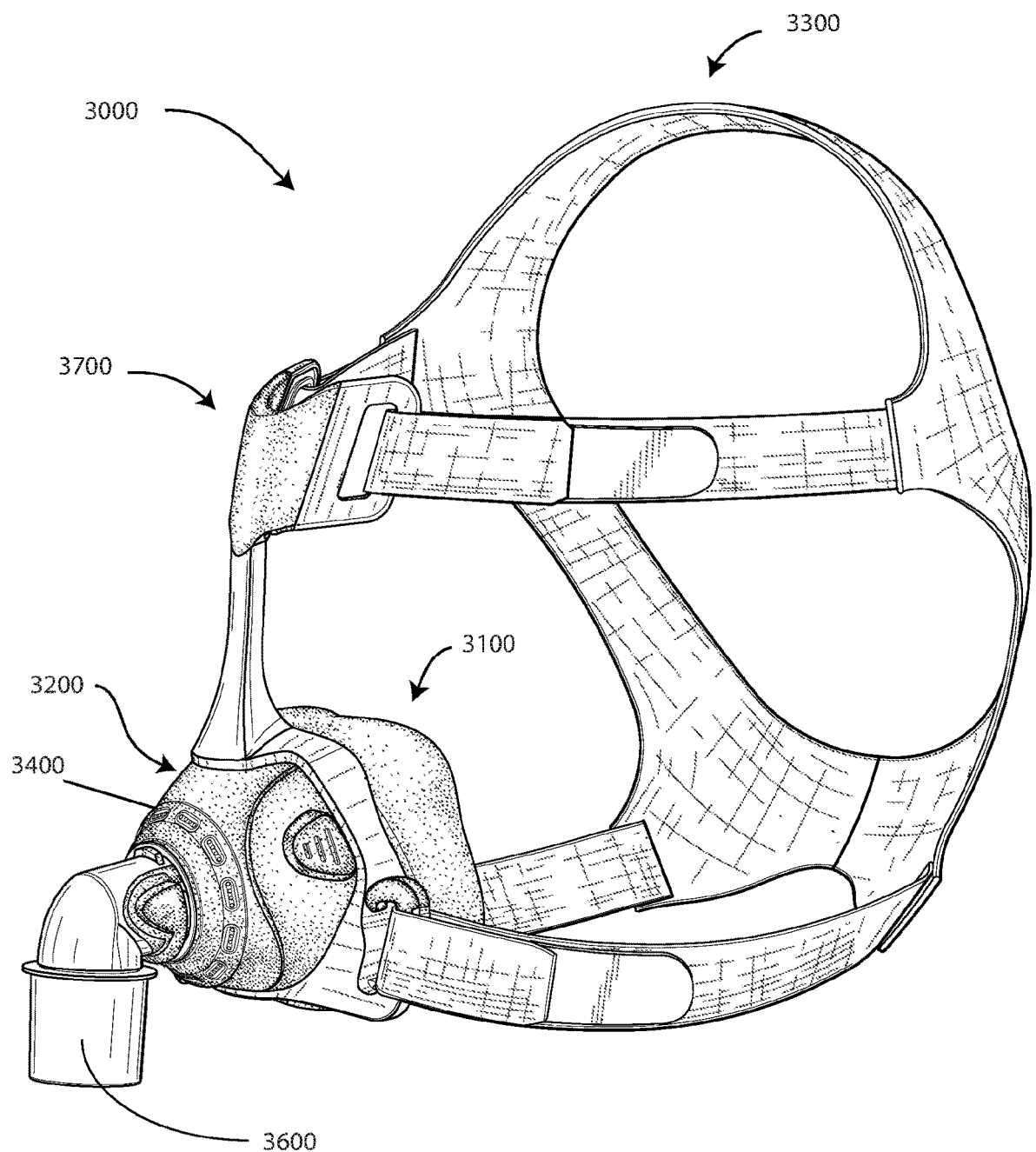

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
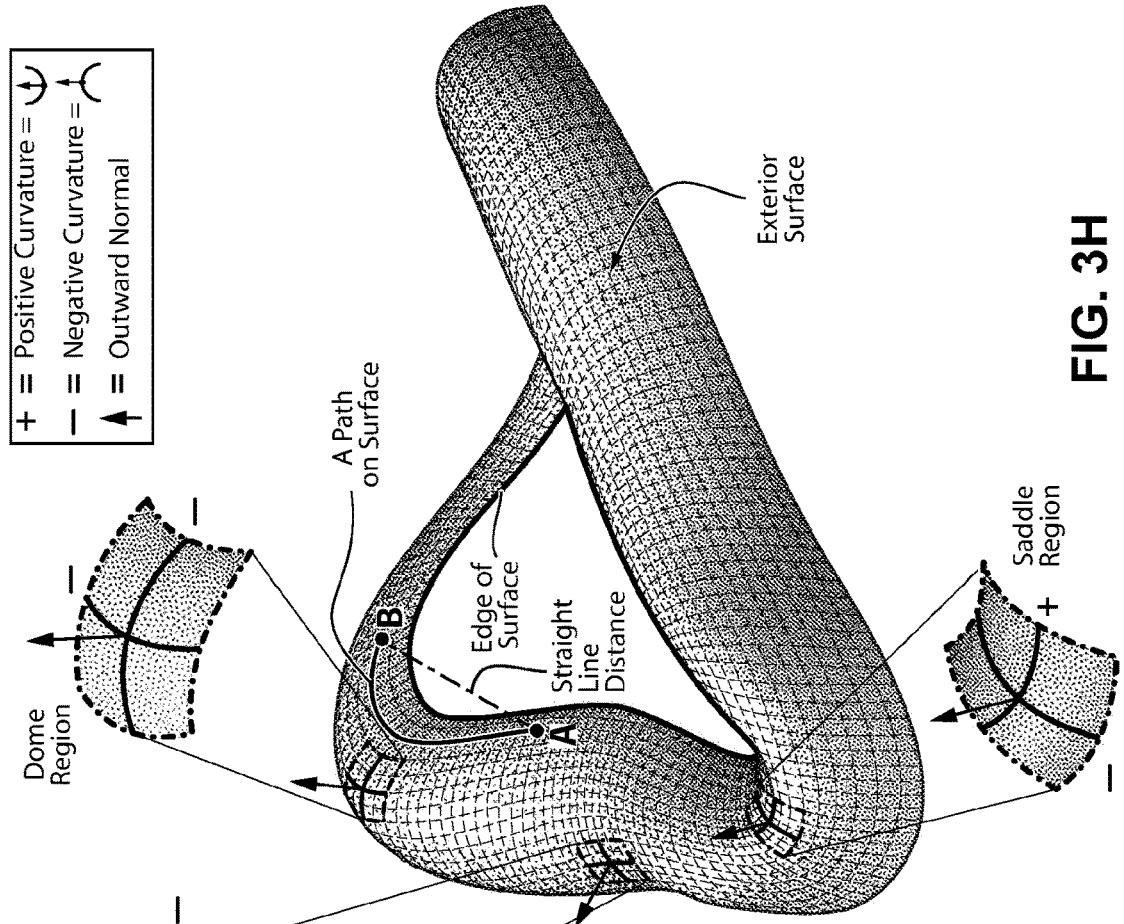
Figure 3G:
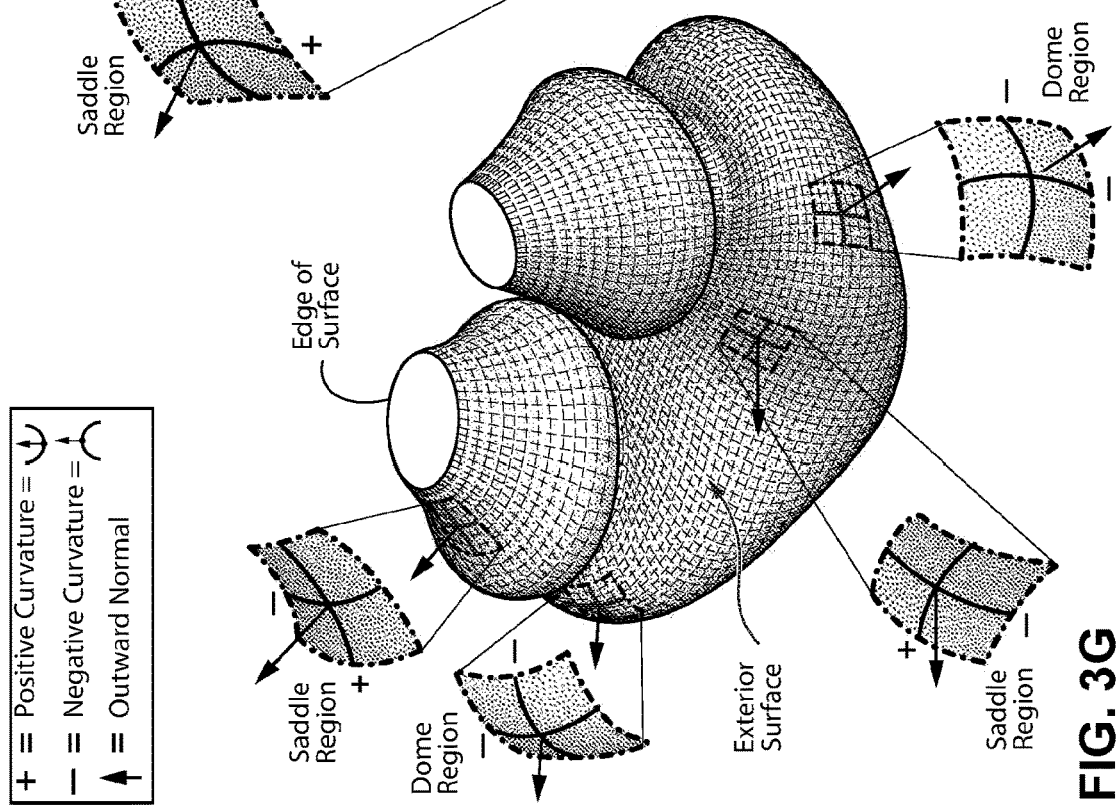

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
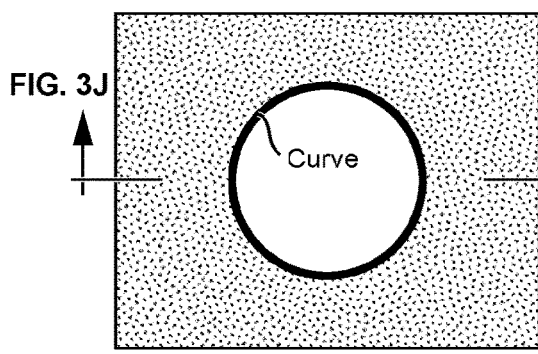

FIG. 3I shows the surface of a structure, with a one dimensional hole in the surface. The illustrated plane curve forms the boundary of a one dimensional hole.

Figure 3K:
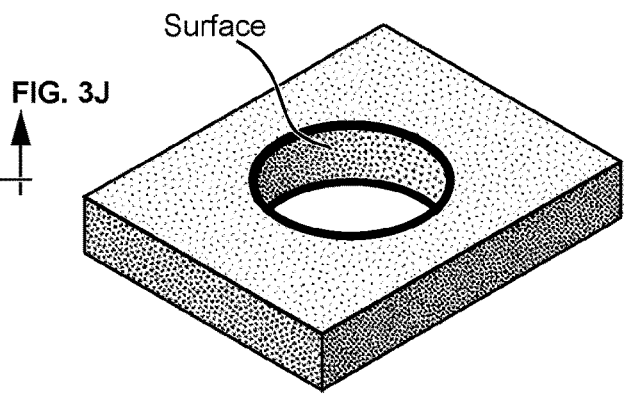
Figure 3J:
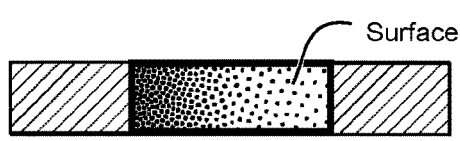

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
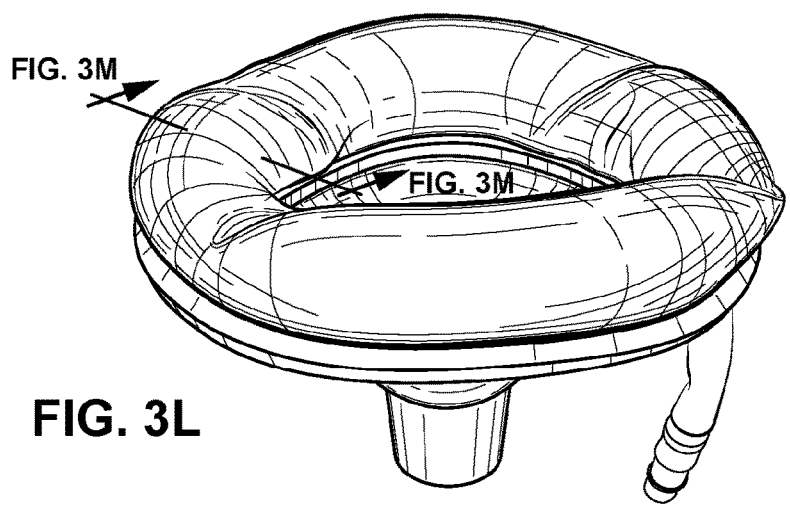

FIG. 3L shows a mask having an inflatable bladder as a cushion.

Figure 3M:
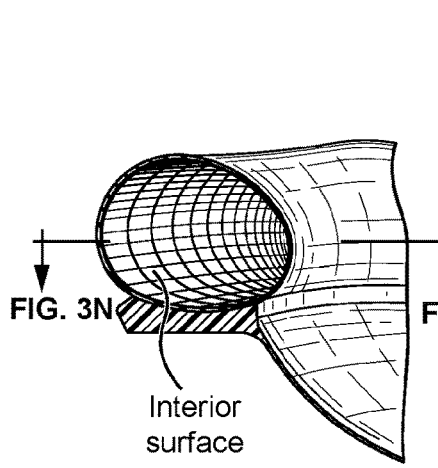

FIG. 3M shows a cross-section through the mask of FIG. 3L, and shows the interior surface of the bladder. The interior surface bounds the two dimensional hole in the mask.

Figure 3N:
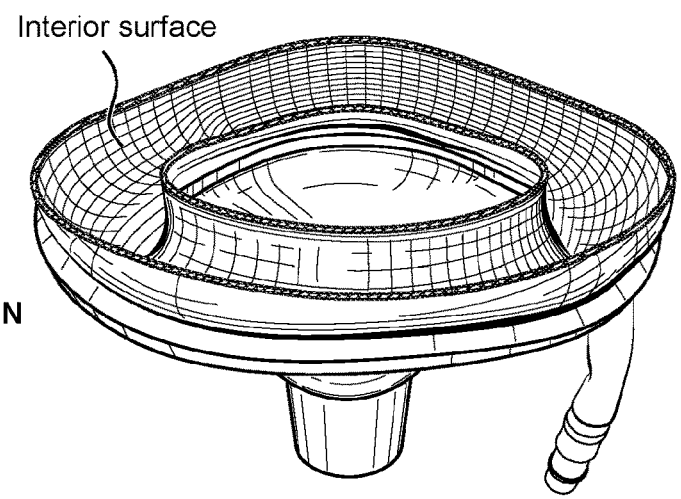

FIG. 3N shows a further cross-section through the mask of FIG. 3L. The interior surface is also indicated.

Figure 3O:
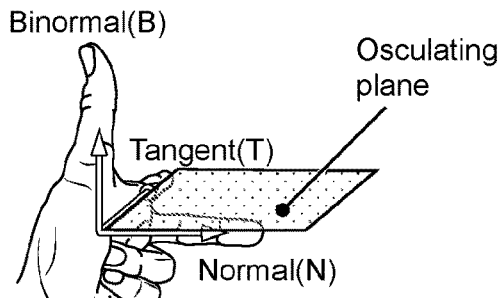

FIG. 3O illustrates a left-hand rule.

Figure 3P:
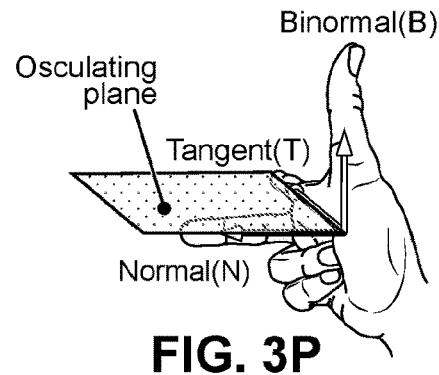

FIG. 3P illustrates a right-hand rule.

Figure 3Q:
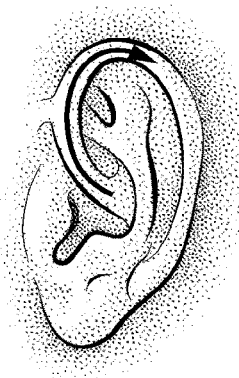

FIG. 3Q shows a left ear, including the left ear helix.

Figure 3S:
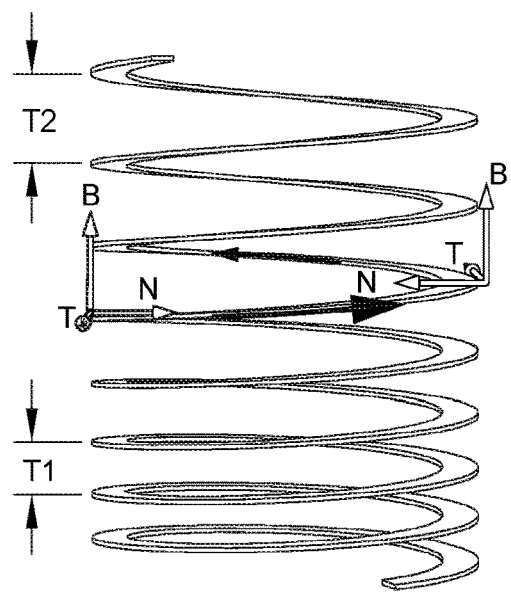
Figure 3R:
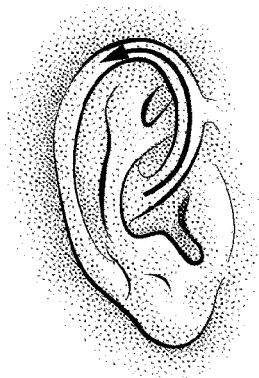

FIG. 3R shows a right ear, including the right ear helix.

FIG. 3S shows a right-hand helix.

Figure 3T:
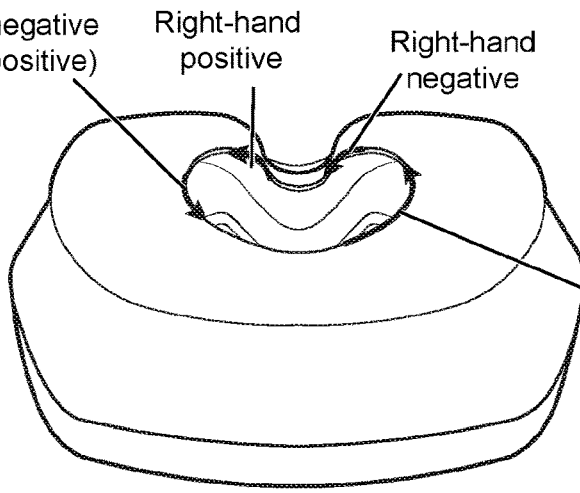

FIG. 3T shows a view of a mask, including the sign of the torsion of the space curve defined by the edge of the sealing membrane in different regions of the mask.

Figure 3U:
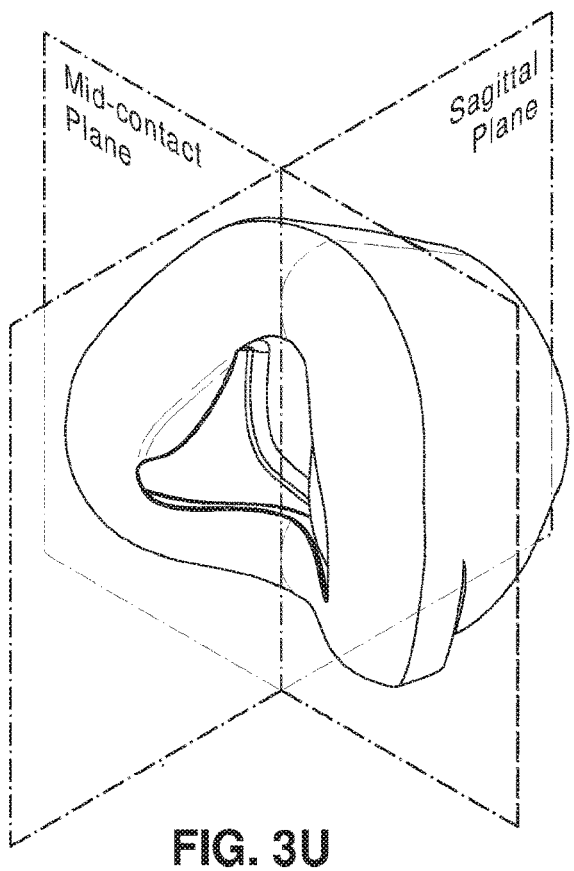

FIG. 3U shows a view of a plenum chamber 3200 showing a sagittal plane and a mid-contact plane.

Figure 3V:
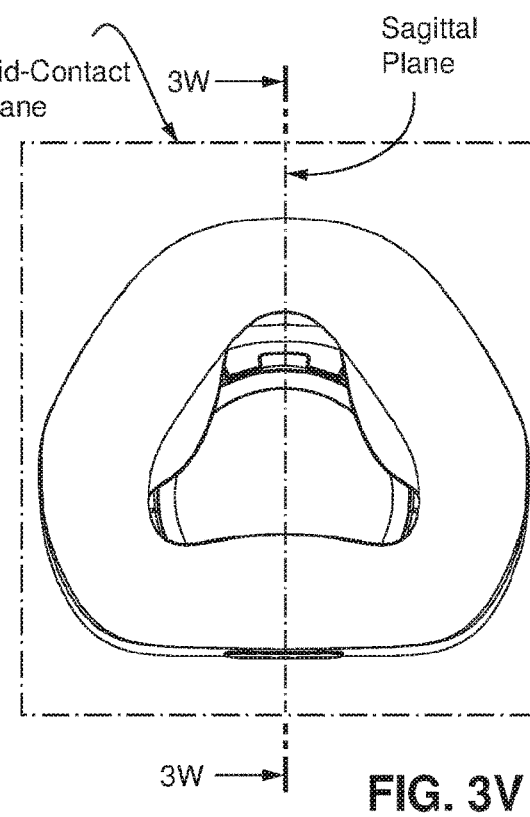

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
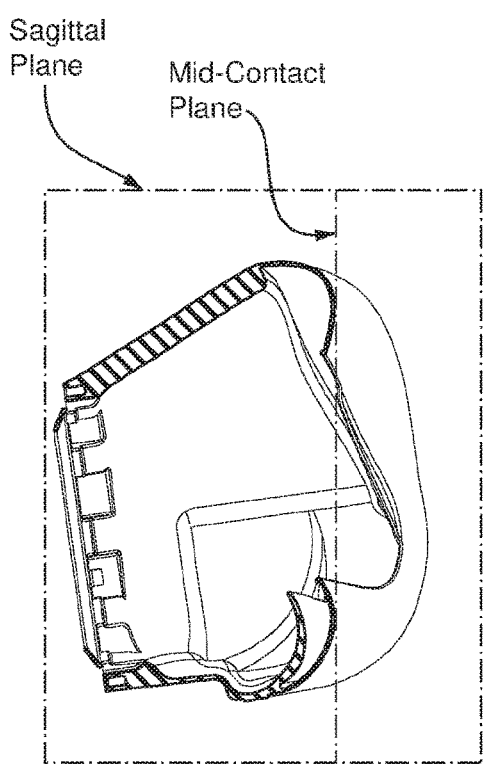

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
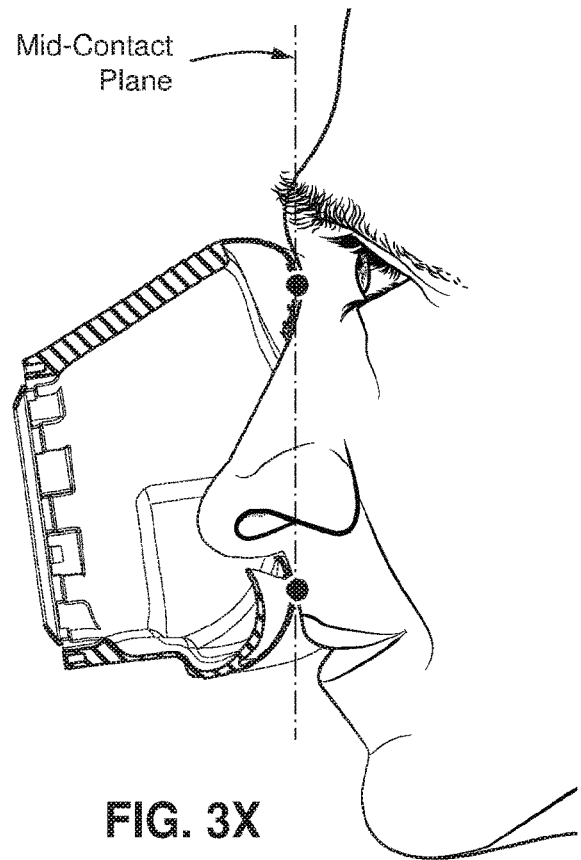

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 4:
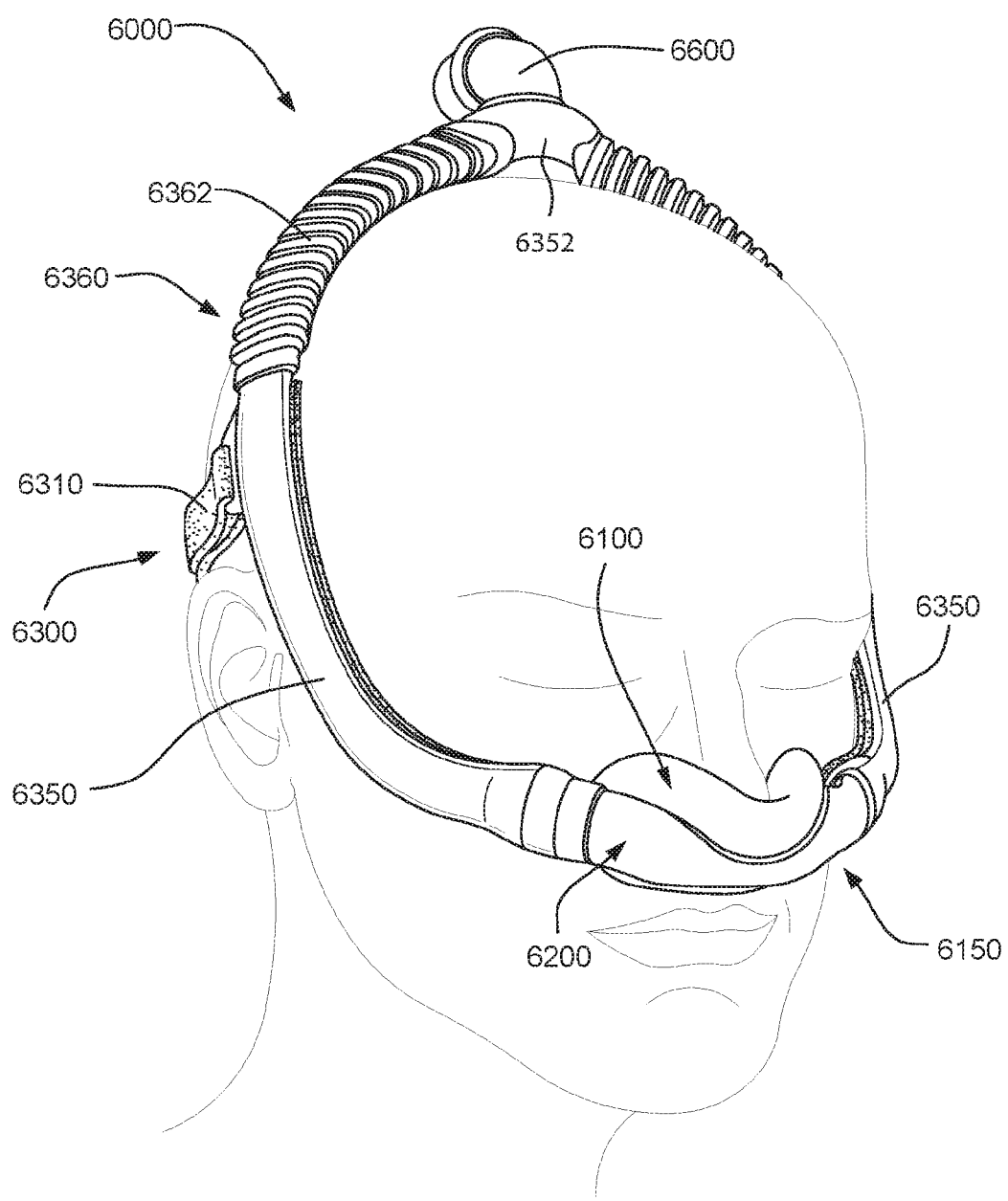

FIG. 4 is a perspective view of a patient interface shown on a patient's head according to an example of the present technology.

Figure 5:
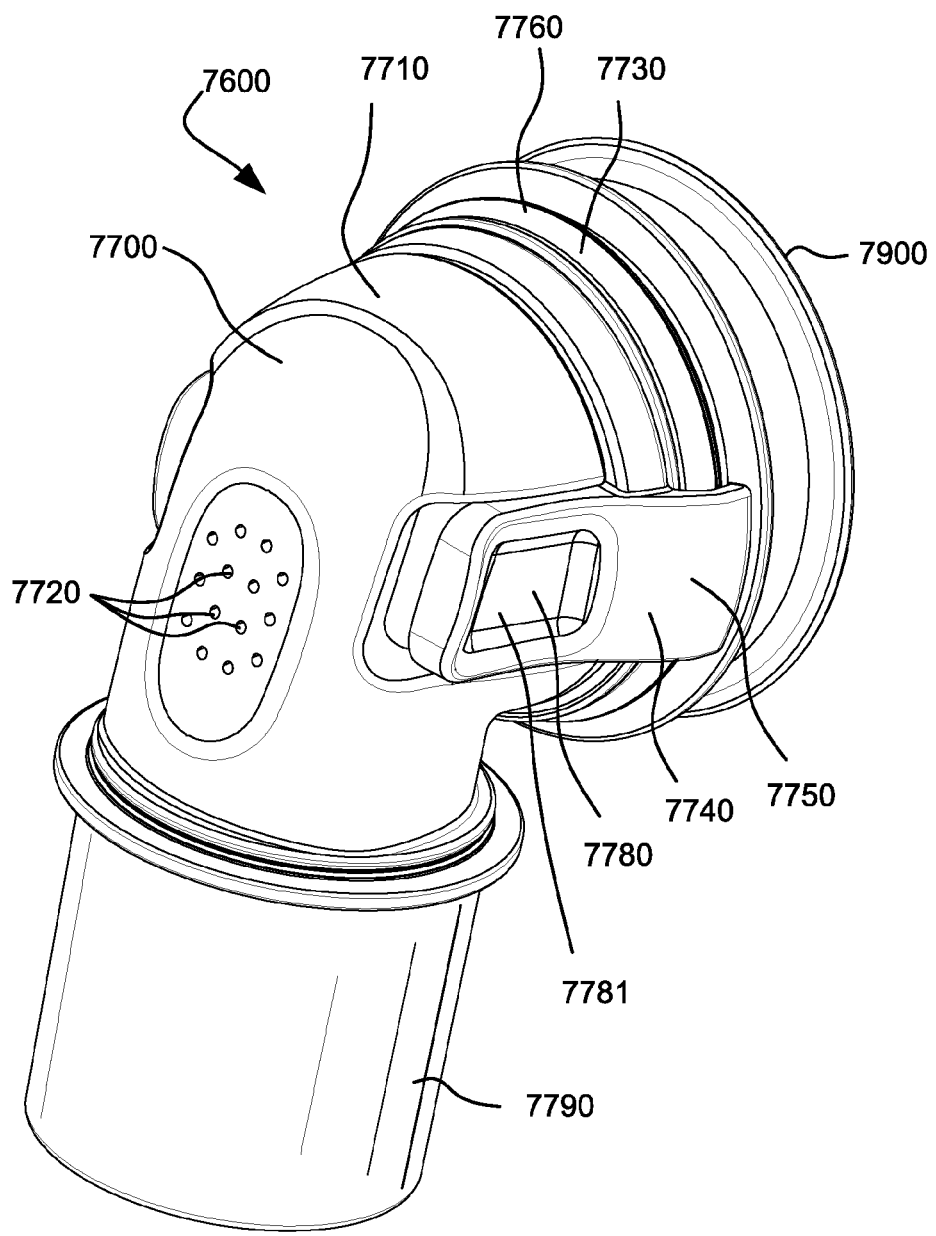

FIG. 5 is a rear perspective view of a connector assembly according to an example of the present technology.

Figure 6:
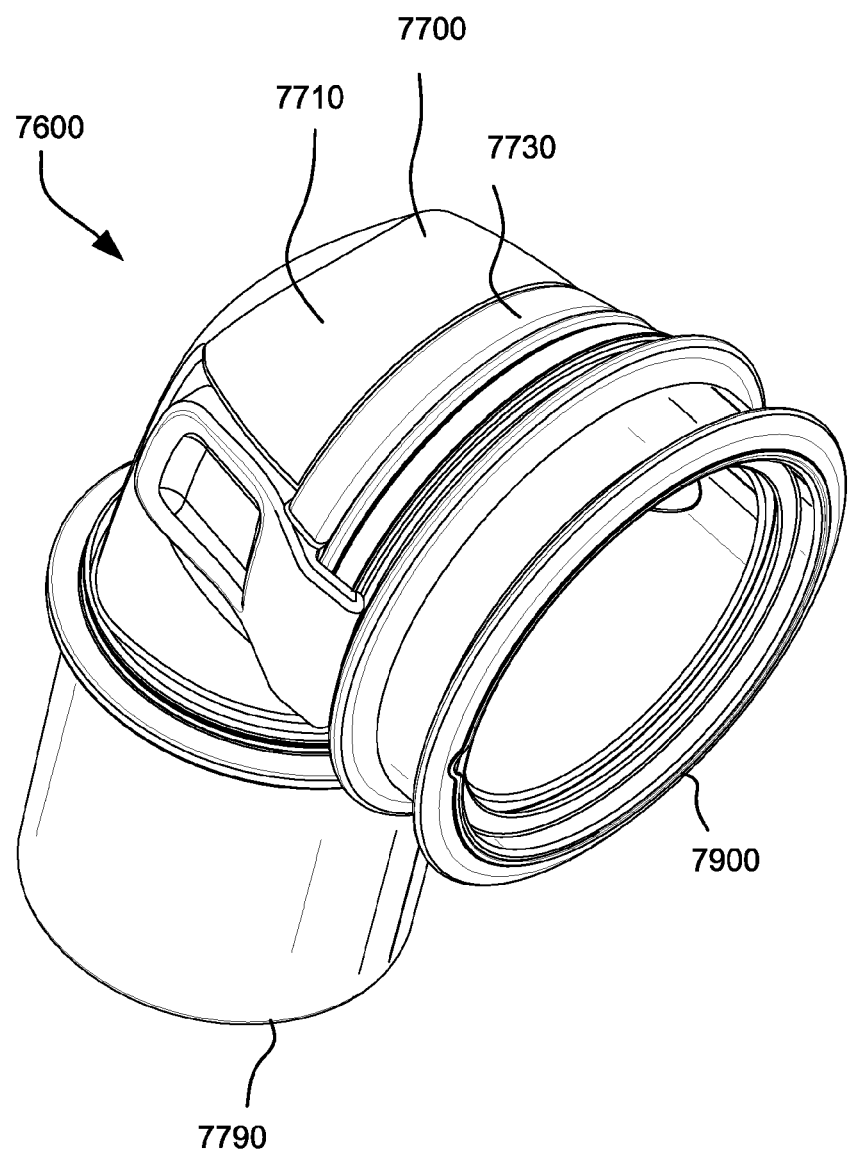

FIG. 6 is a front perspective view of the connector assembly shown in FIG. 5.

Figure 7:
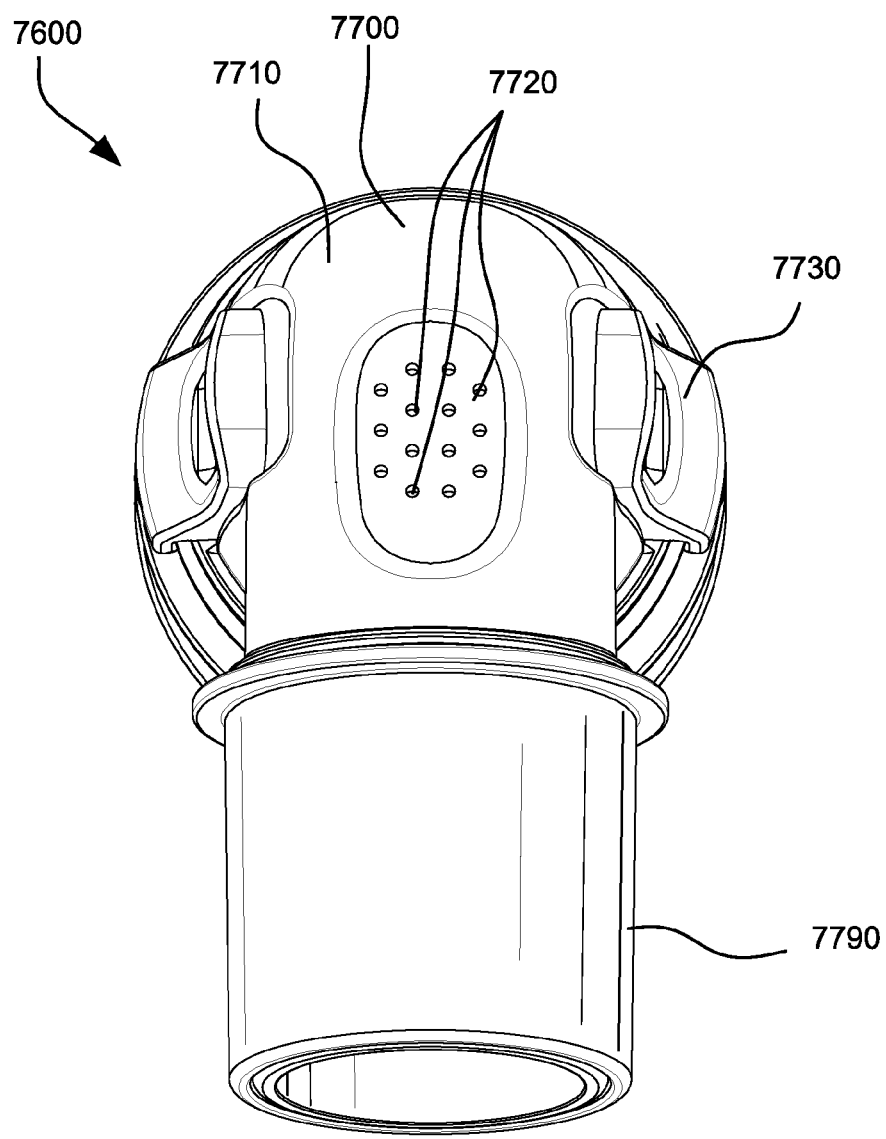

FIG. 7 is a rear view of the connector assembly shown in FIG. 5.

Figure 8:
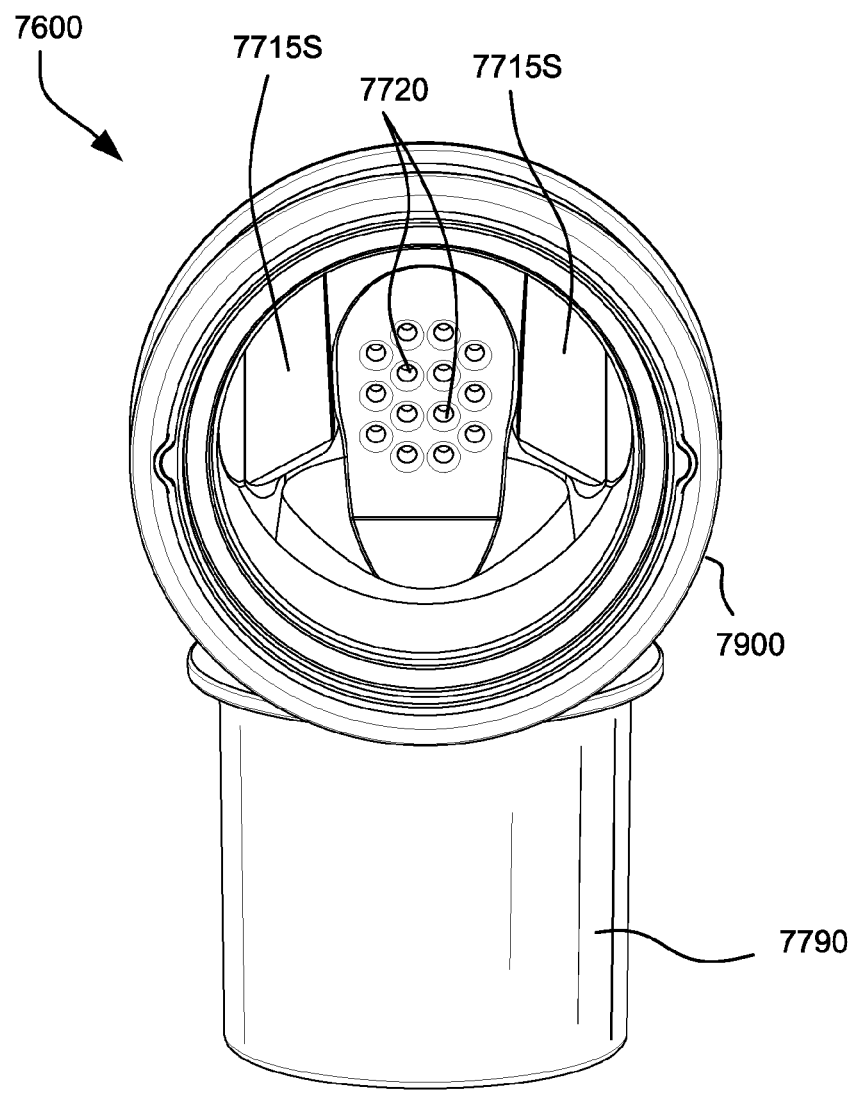

FIG. 8 is a front view of the connector assembly shown in FIG. 5.

Figure 9:
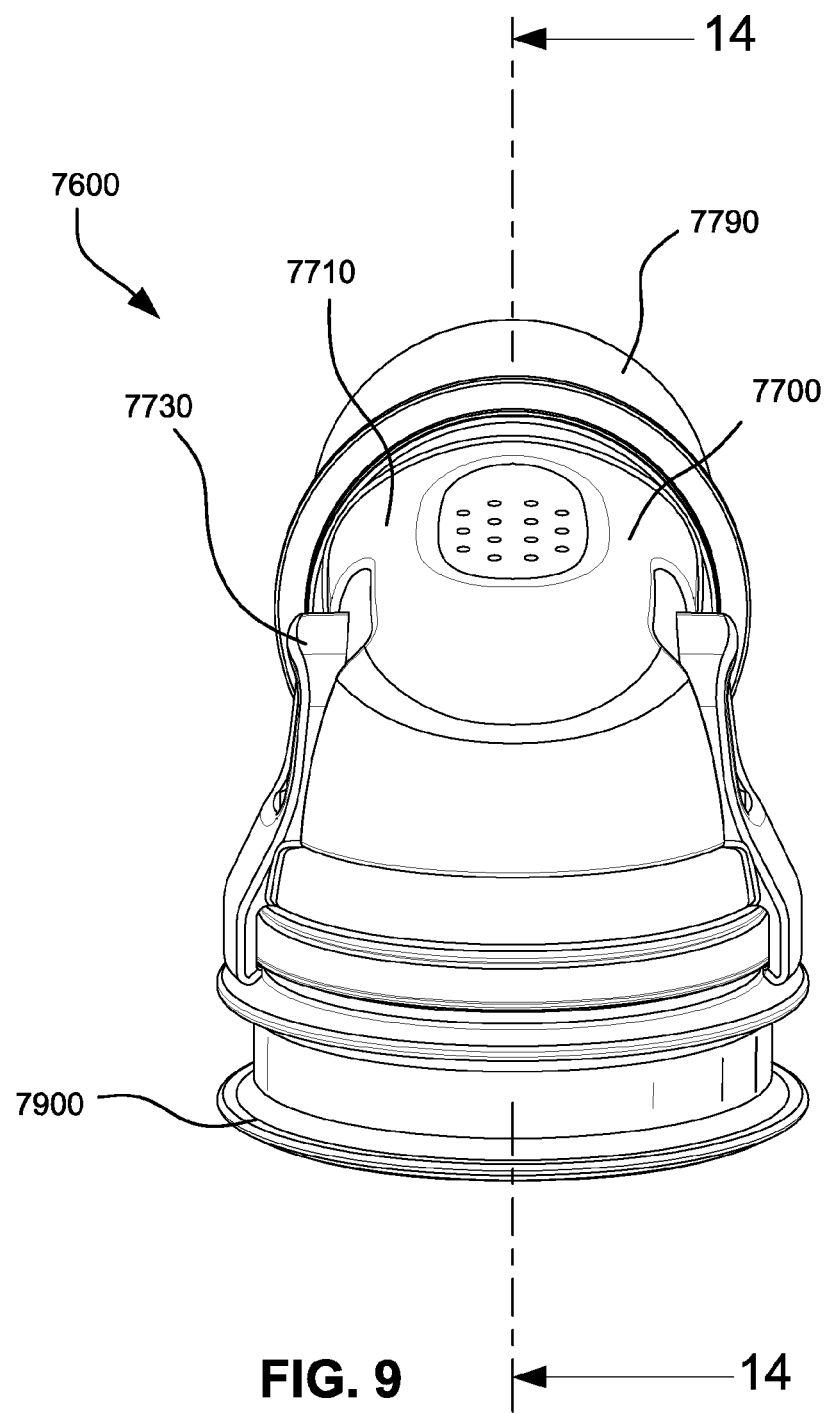

FIG. 9 is a top view of the connector assembly shown in FIG. 5.

Figure 10:
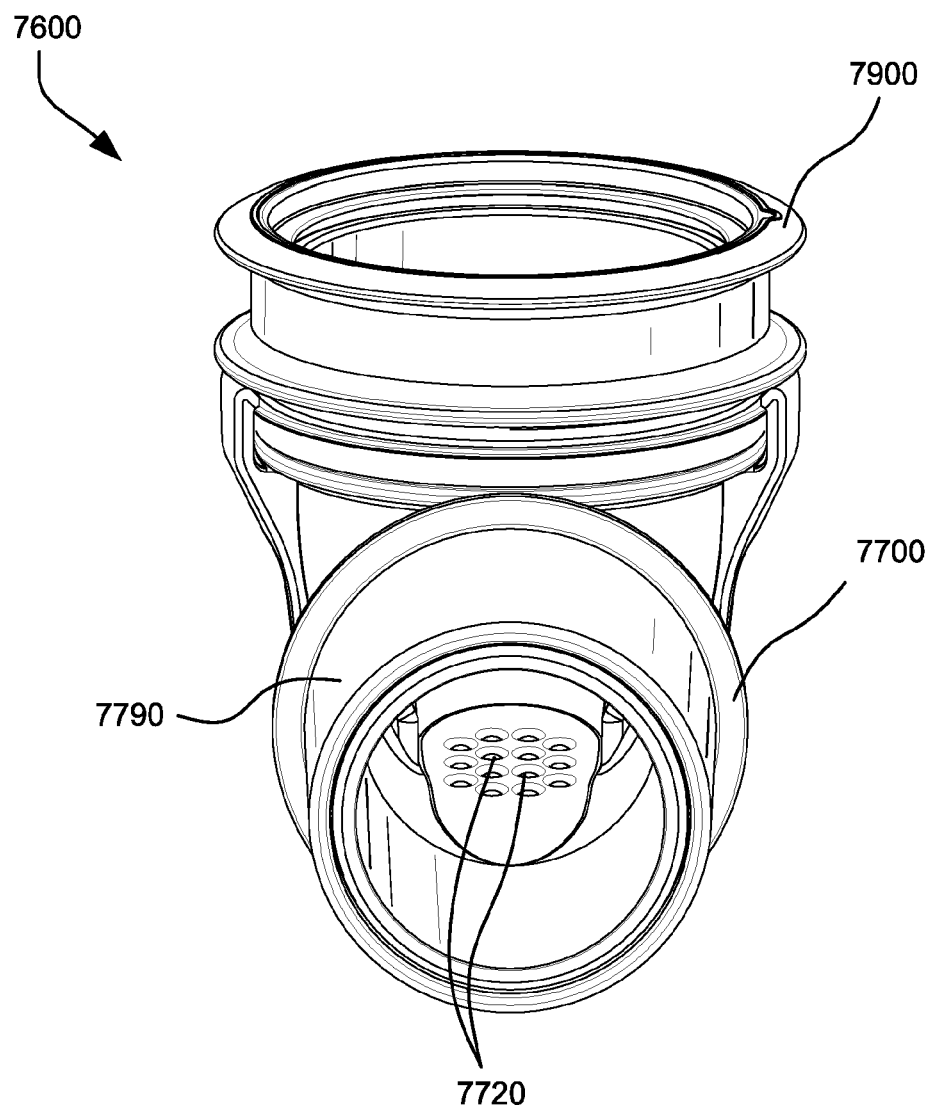

FIG. 10 is a bottom view of the connector assembly shown in FIG. 5.

Figure 11:
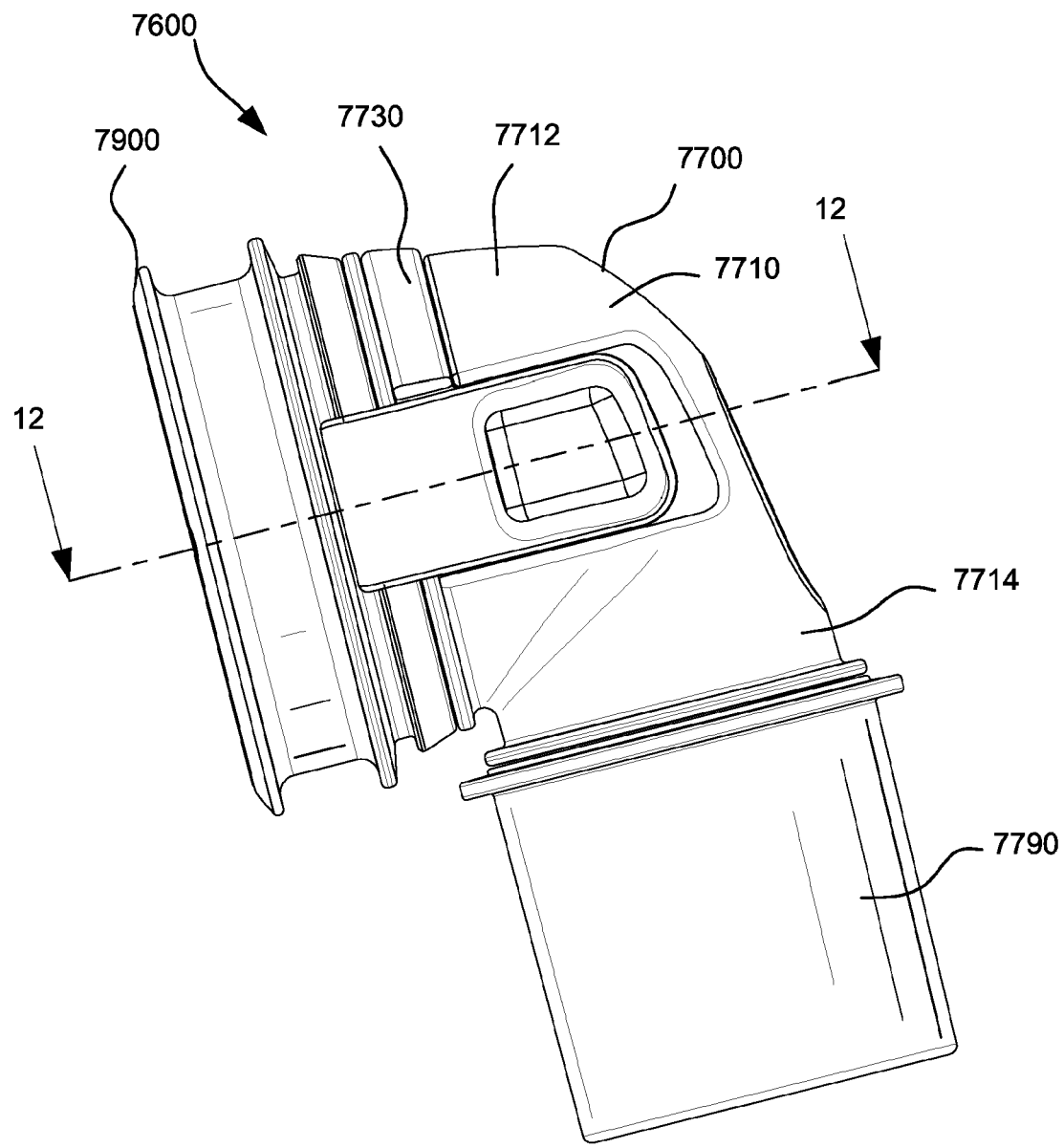

FIG. 11 is a side view of the connector assembly shown in FIG. 5.

Figure 12:
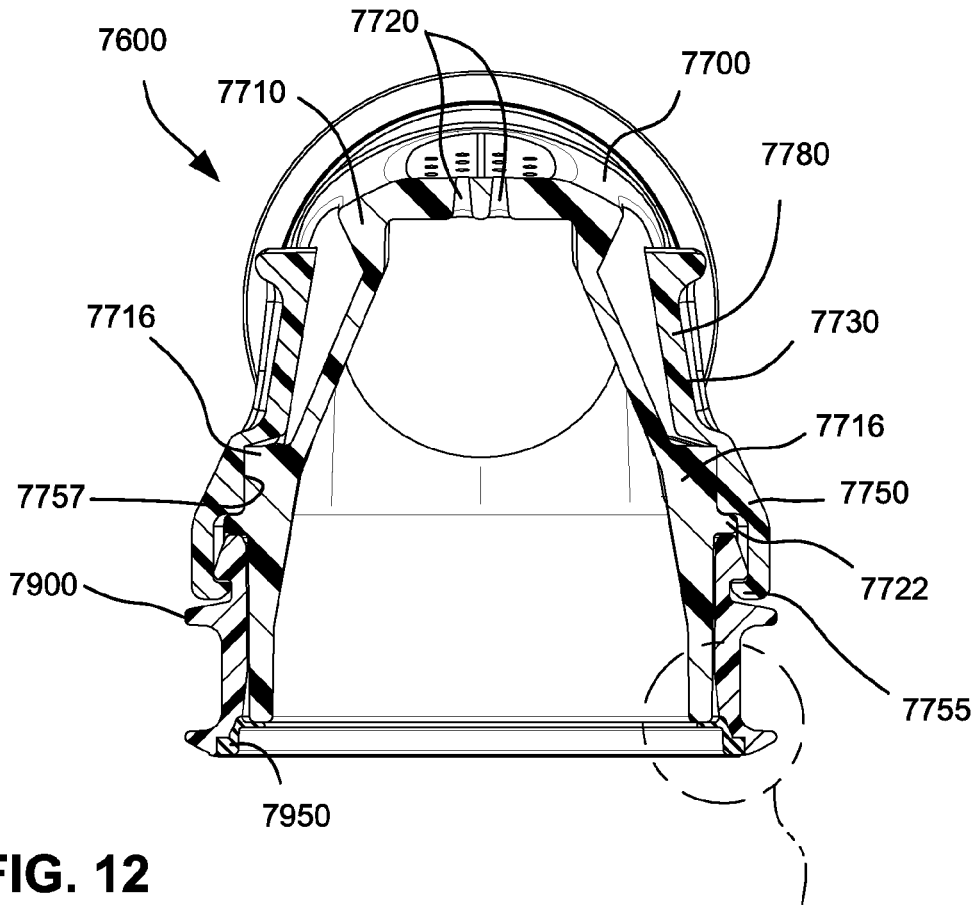

FIG. 12 is a cross-sectional view of the connector assembly shown in FIG. 11.

Figure 13:
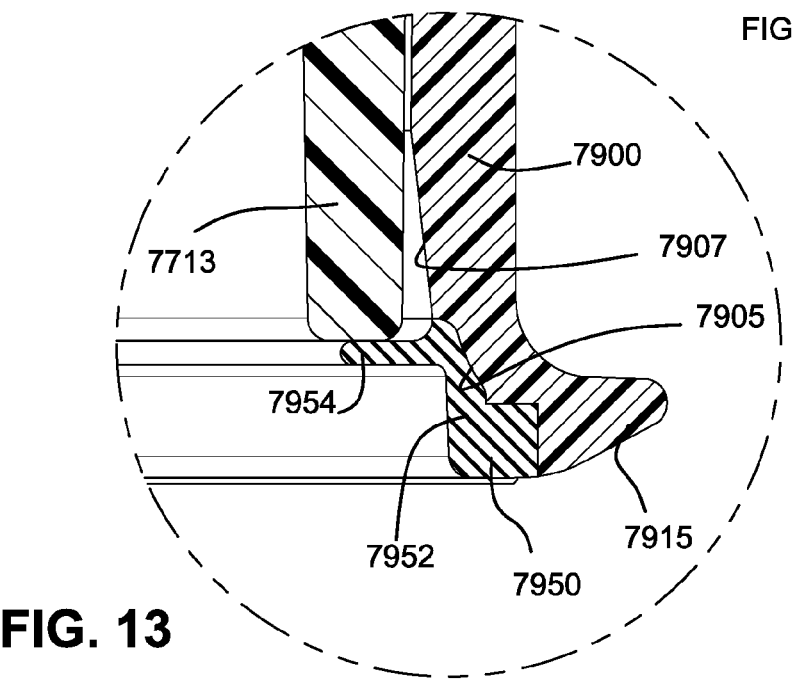

FIG. 13 is an enlarged portion of the cross-section of FIG. 12.

Figure 14:
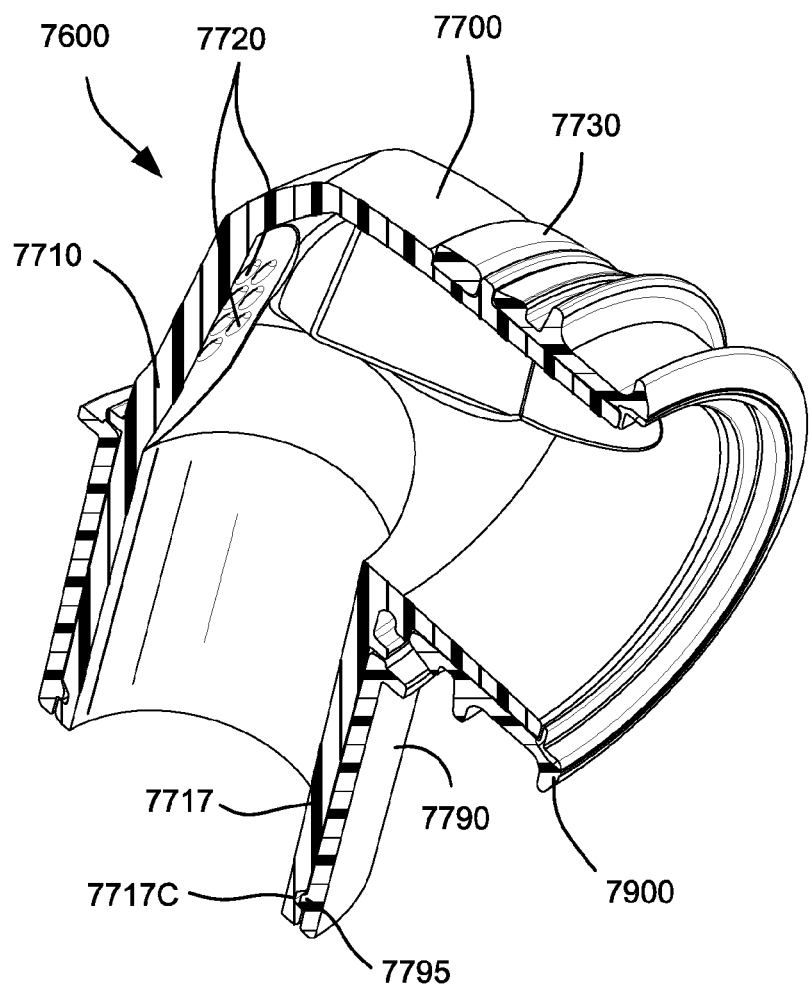

FIG. 14 is a cross-sectional view of the connector assembly shown in FIG. 9.

Figure 15:
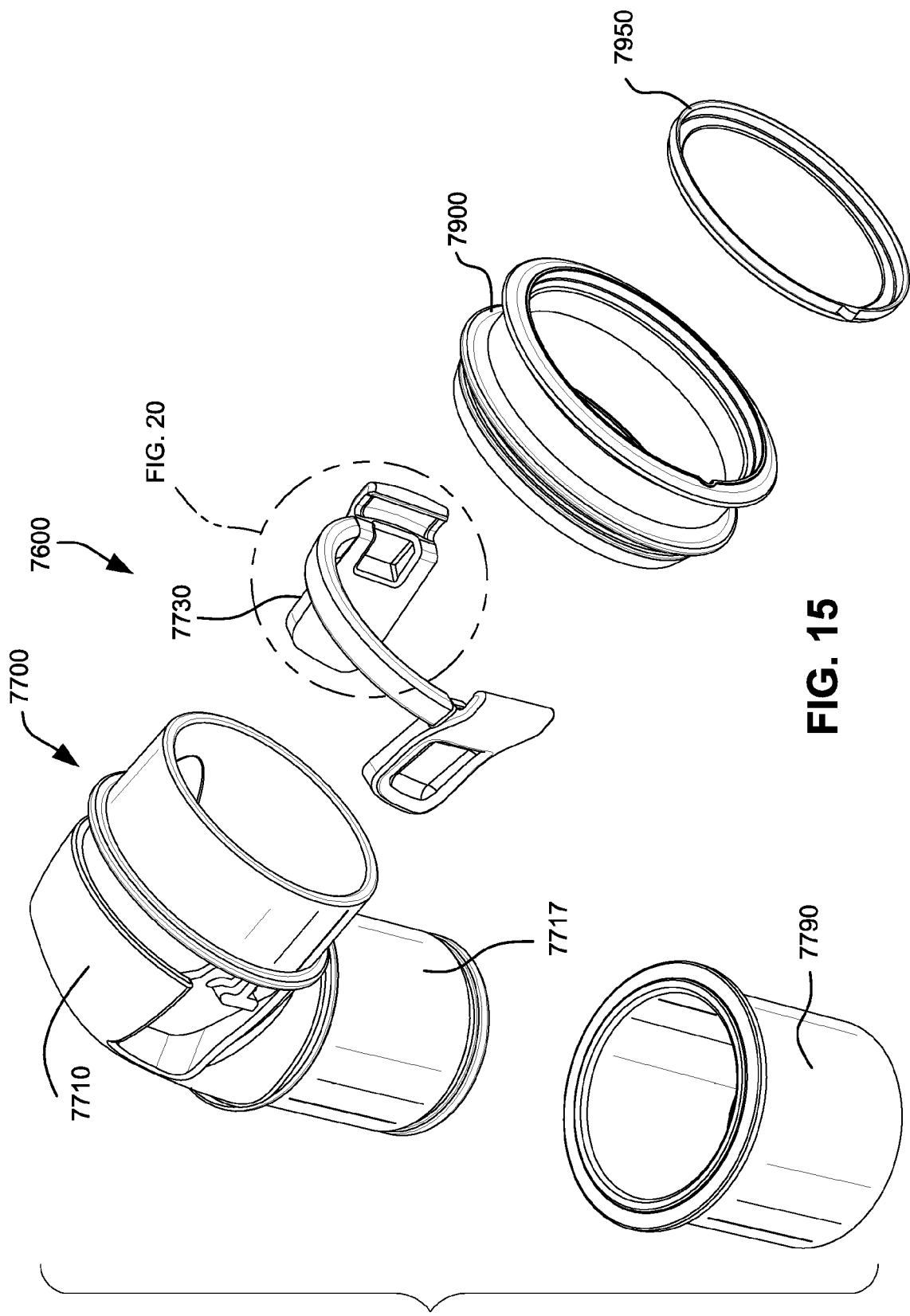

FIG. 15 is an exploded view of the connector assembly shown in FIG. 5.

Figure 16:
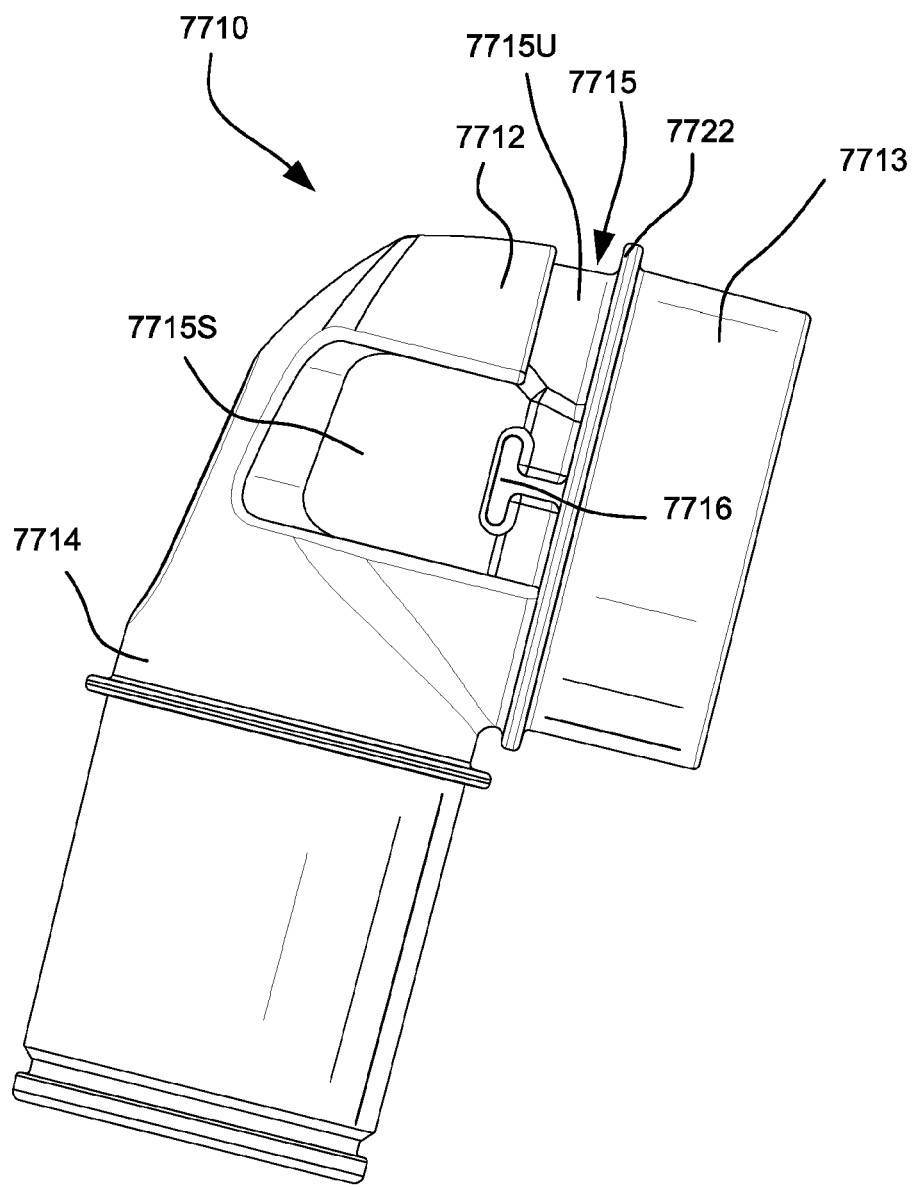

FIG. 16 is a side view of an elbow member of the connector assembly shown in FIG. 5.

Figure 17:
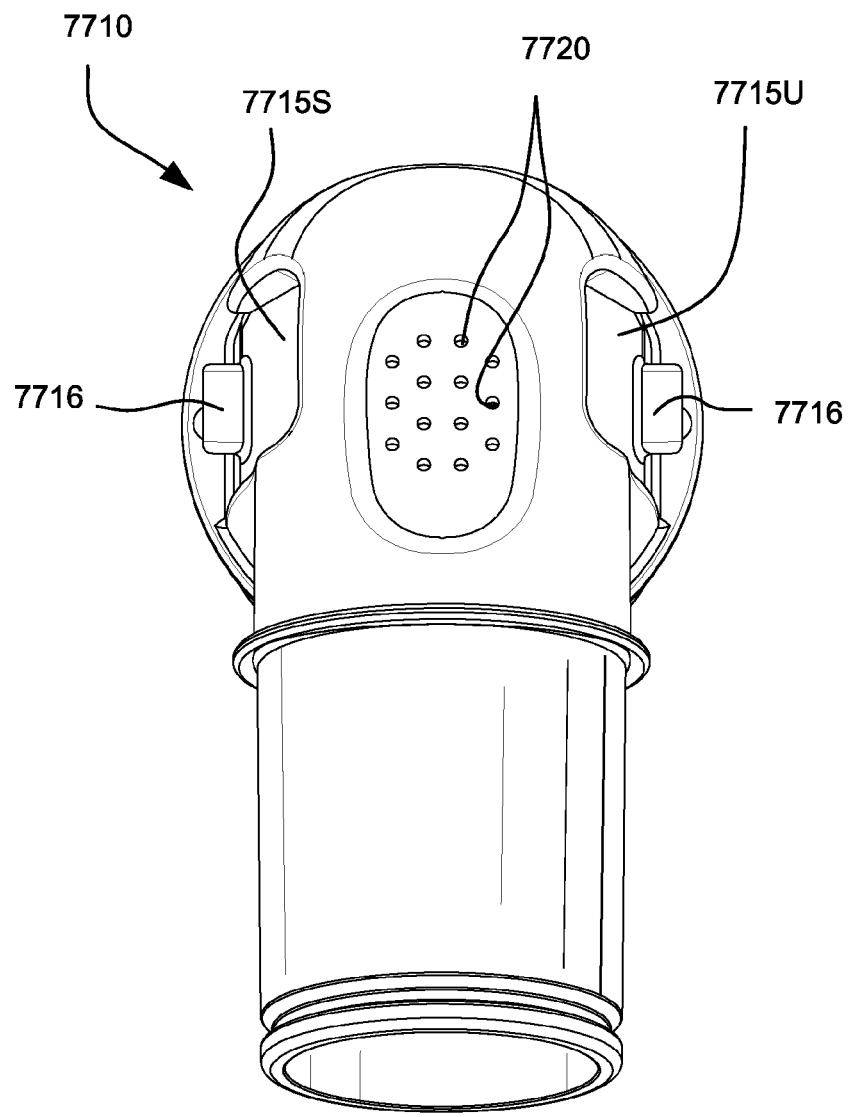

FIG. 17 is a rear view of the elbow member shown in FIG. 16.

Figure 18:
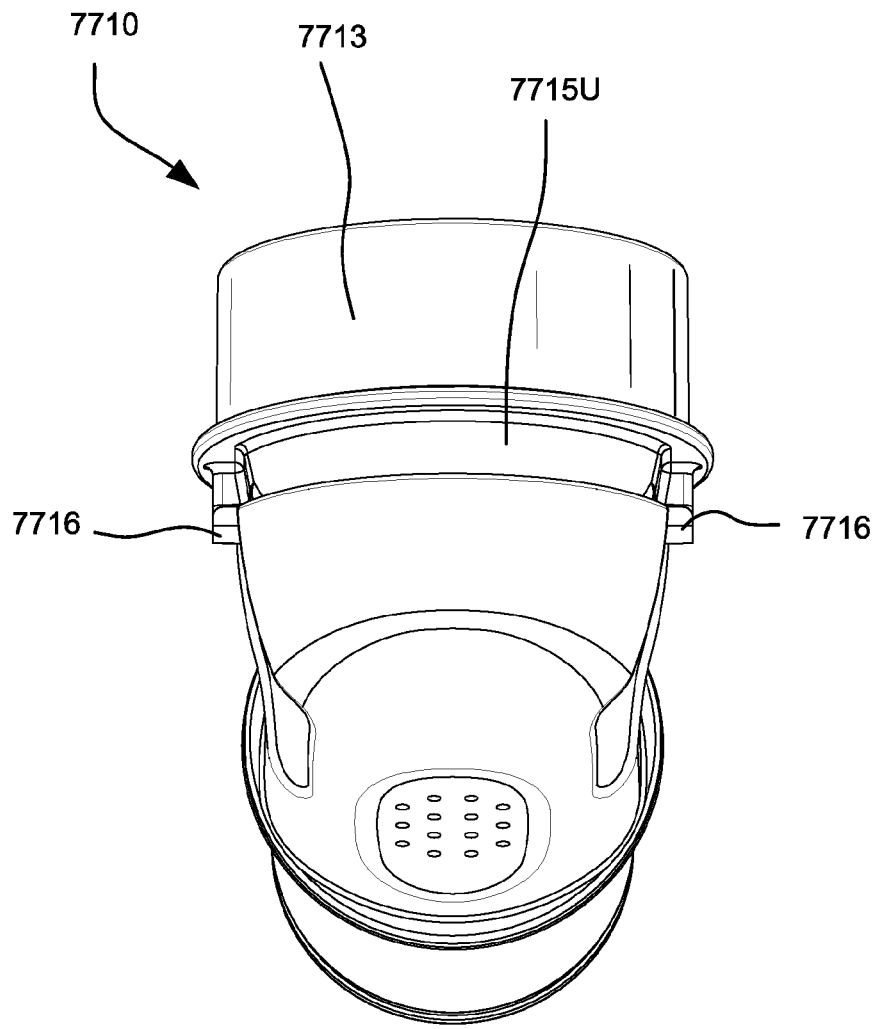

FIG. 18 is a top view of the elbow member shown in FIG. 16.

Figure 19:
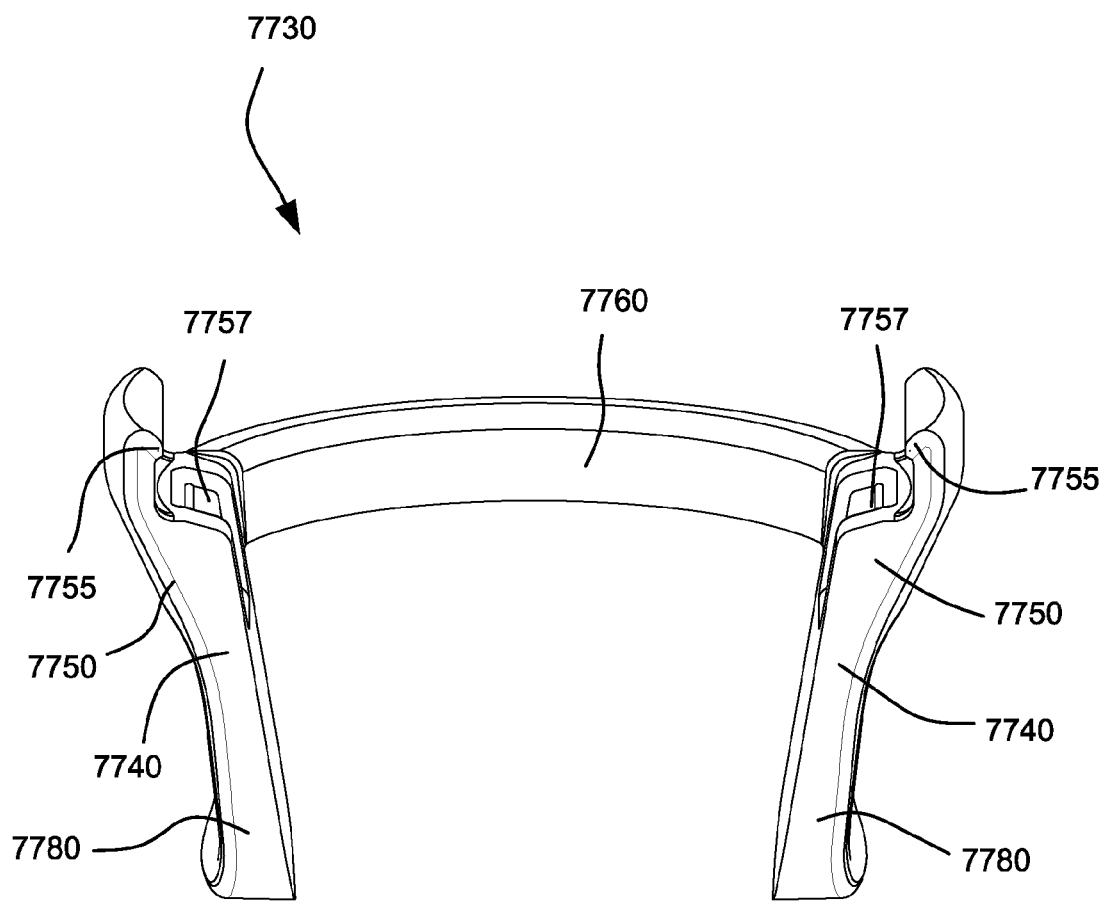

FIG. 19 is a bottom view of a clip member of the connector assembly shown in FIG. 5.

Figure 20:
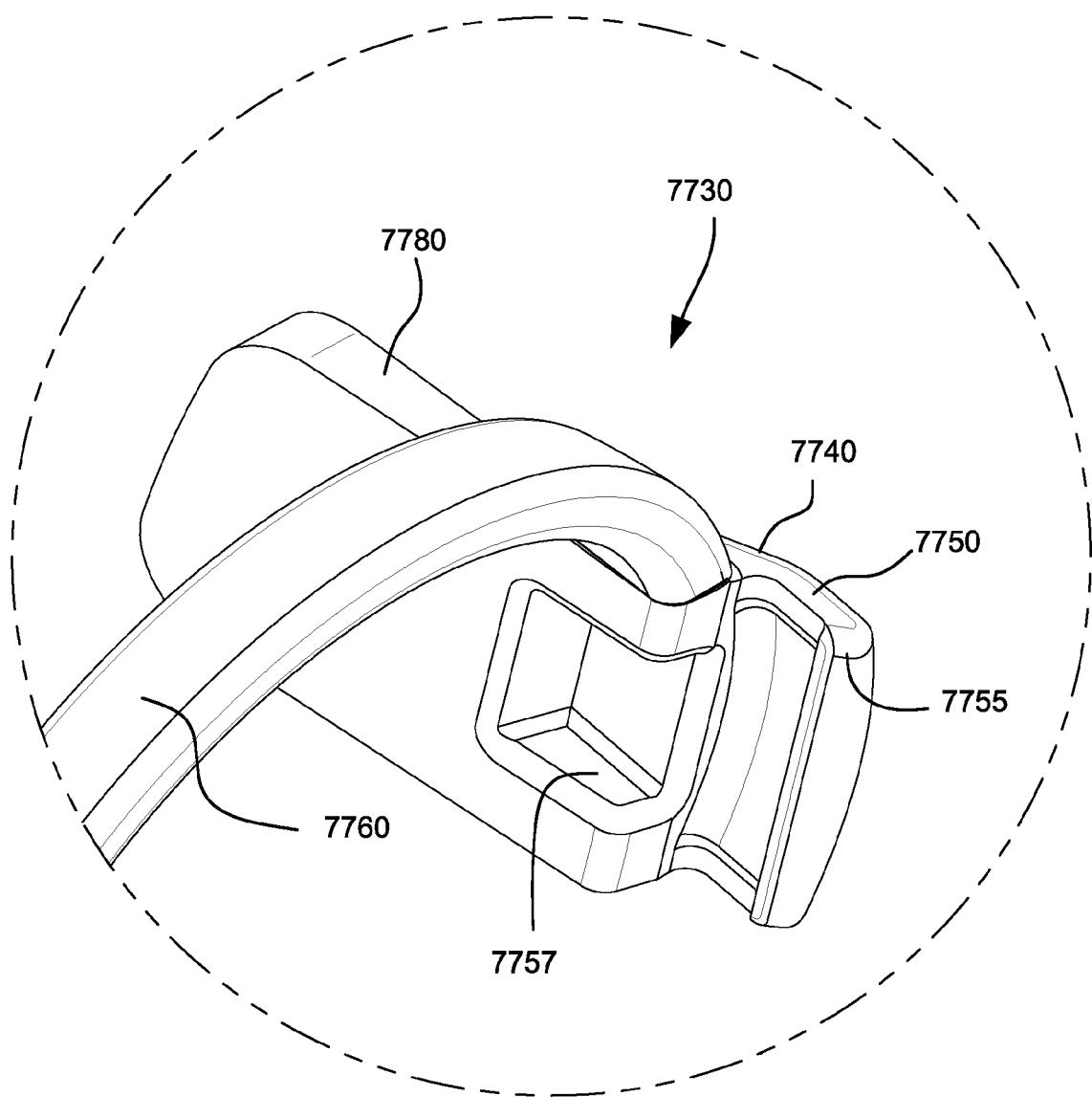

FIG. 20 is an enlarged portion of the clip member shown in FIG. 15.

Figure 21:
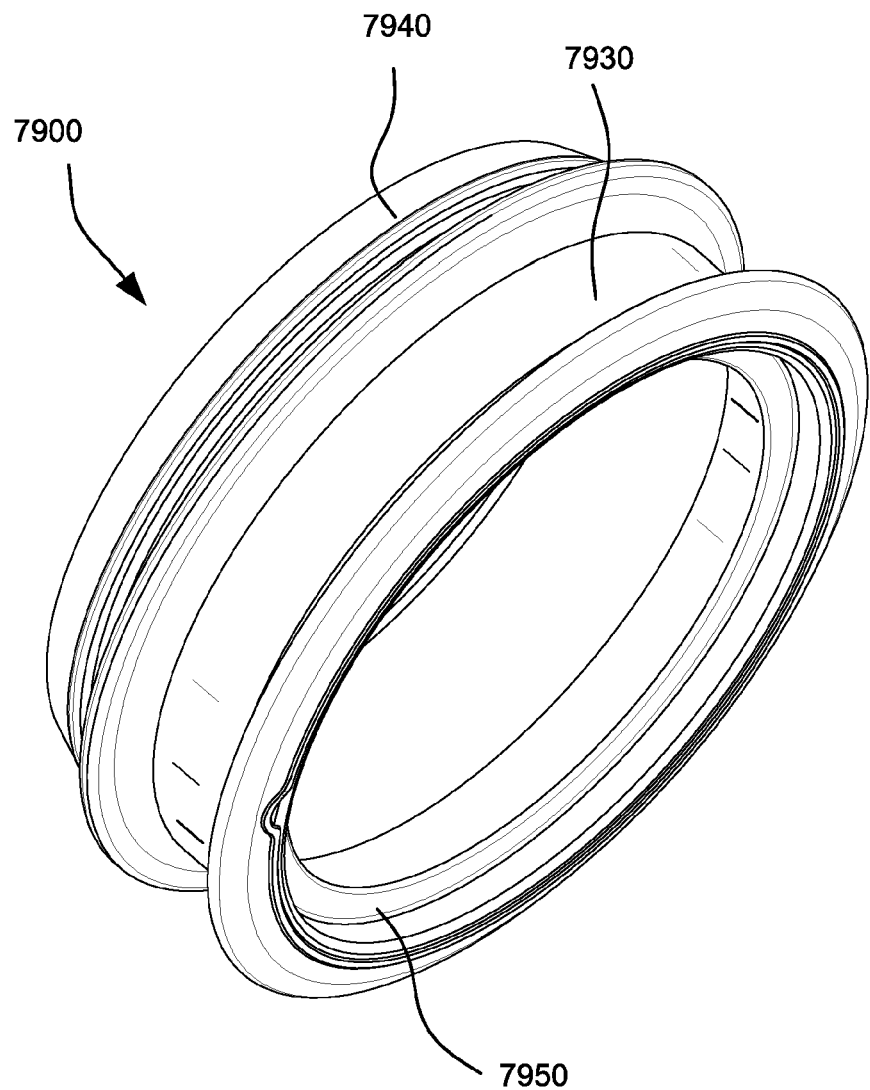

FIG. 21 is a perspective view of a ring member of the connector assembly shown in FIG. 5.

Figure 22:
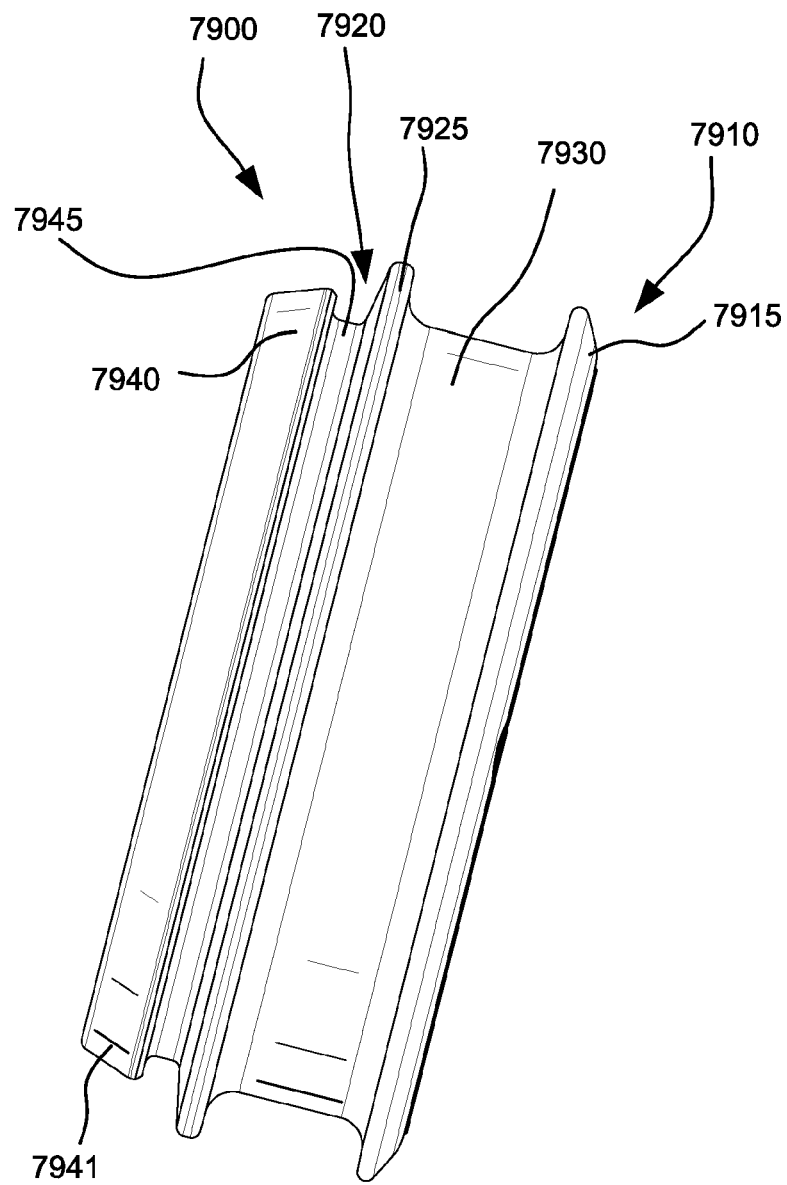

FIG. 22 is a side view of the ring member shown in FIG. 21.

Figure 23:
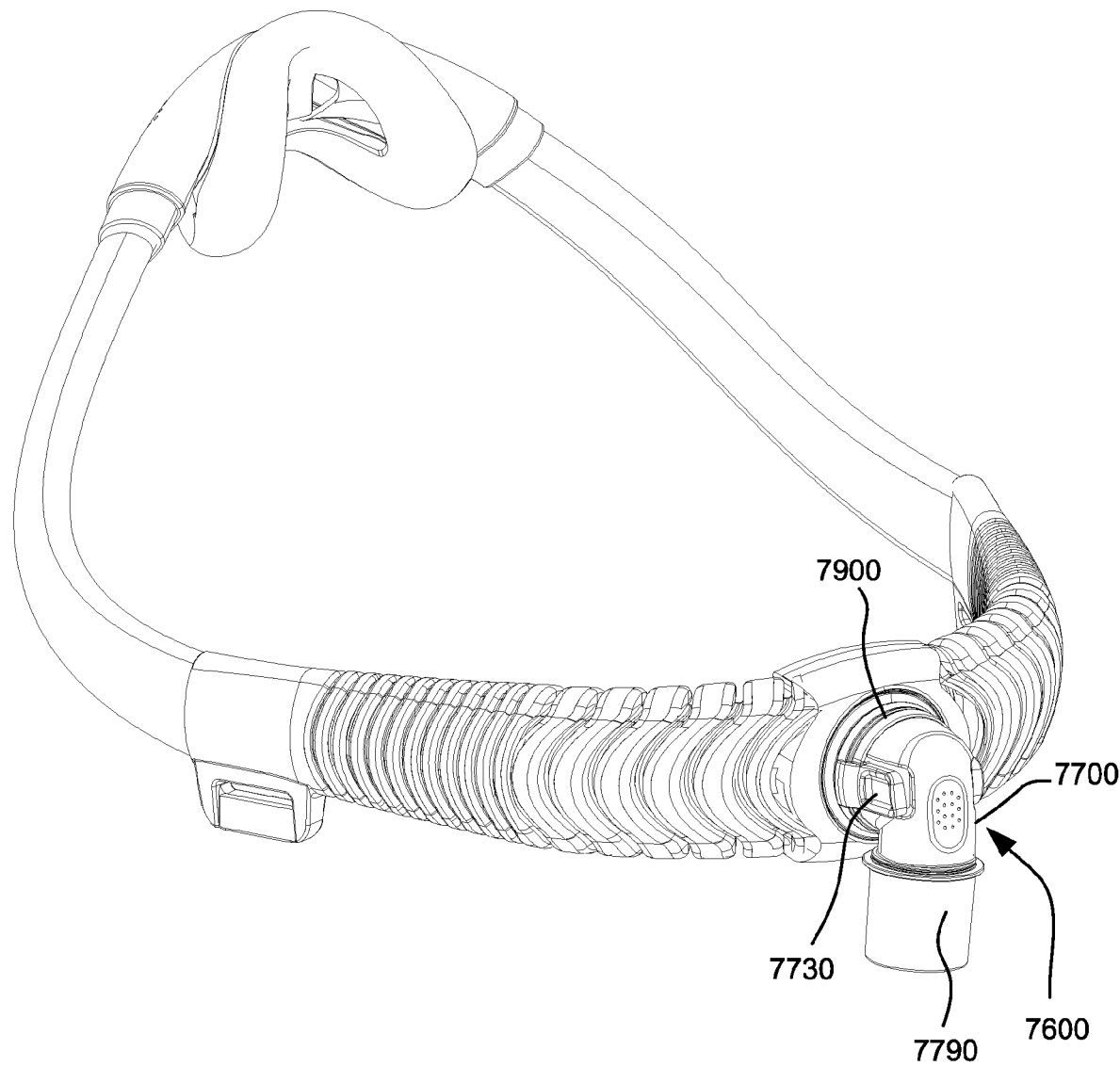

FIG. 23 is a perspective view of a patient interface including a connector assembly according to an example of the present technology with the elbow assembly engaged with the ring member.

Figure 24:
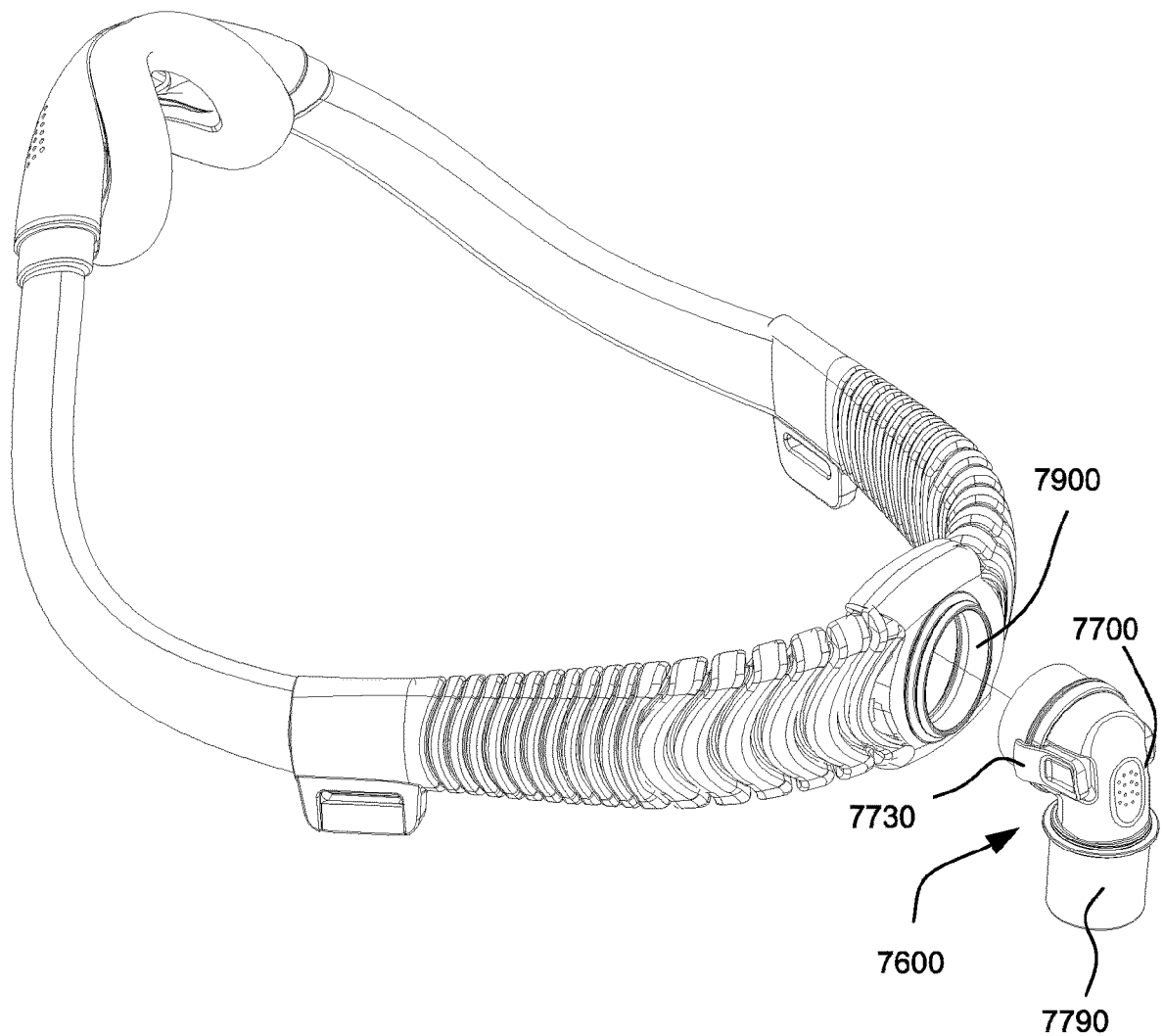

FIG. 24 is a perspective view of a patient interface including a connector assembly according to an example of the present technology with the elbow assembly disengaged from the ring member.

Figure 25:
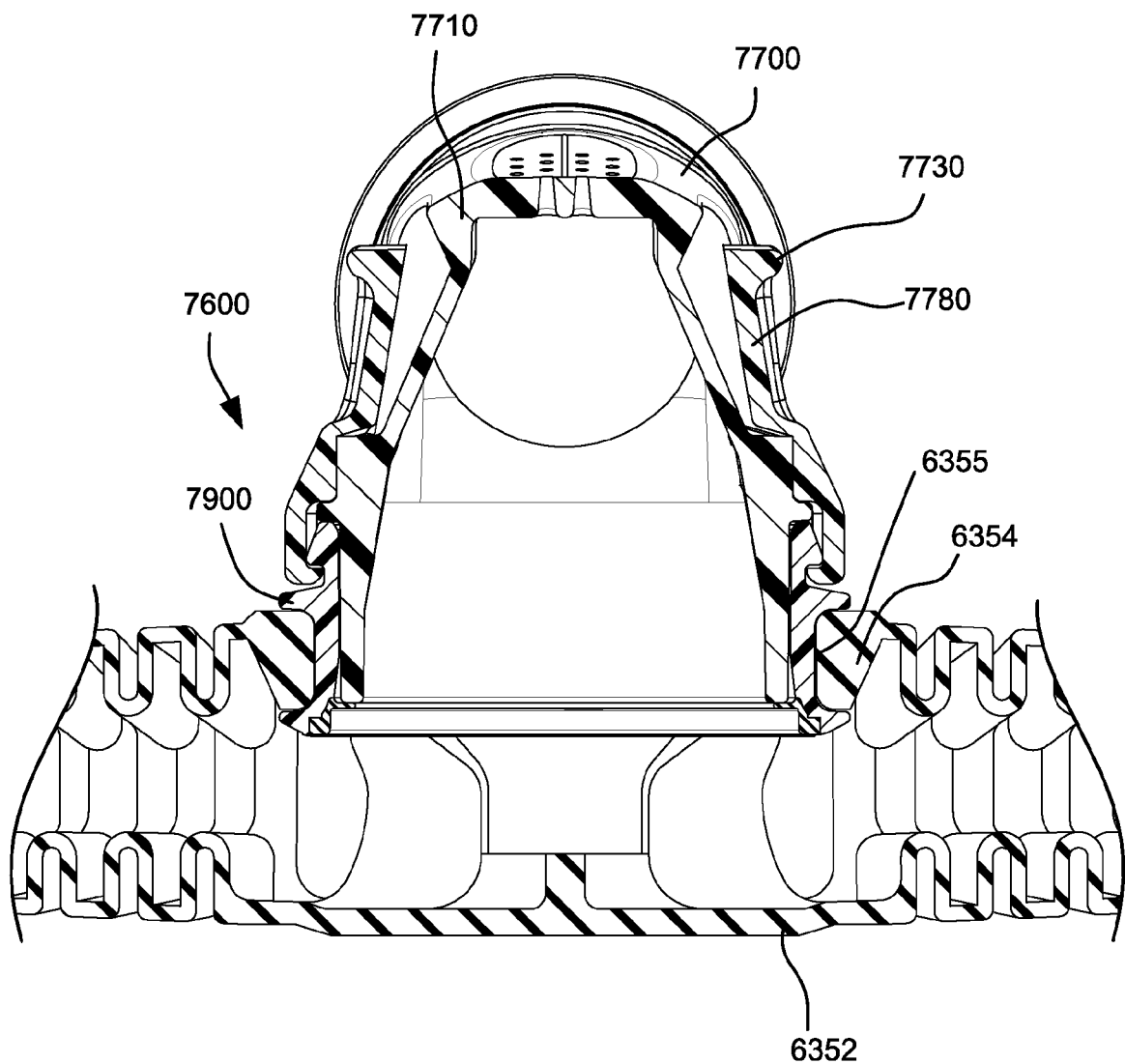

FIG. 25 is a cross-sectional view of a patient interface including a connector assembly according to an example of the present technology with the elbow assembly engaged with the ring member.

Figure 26:
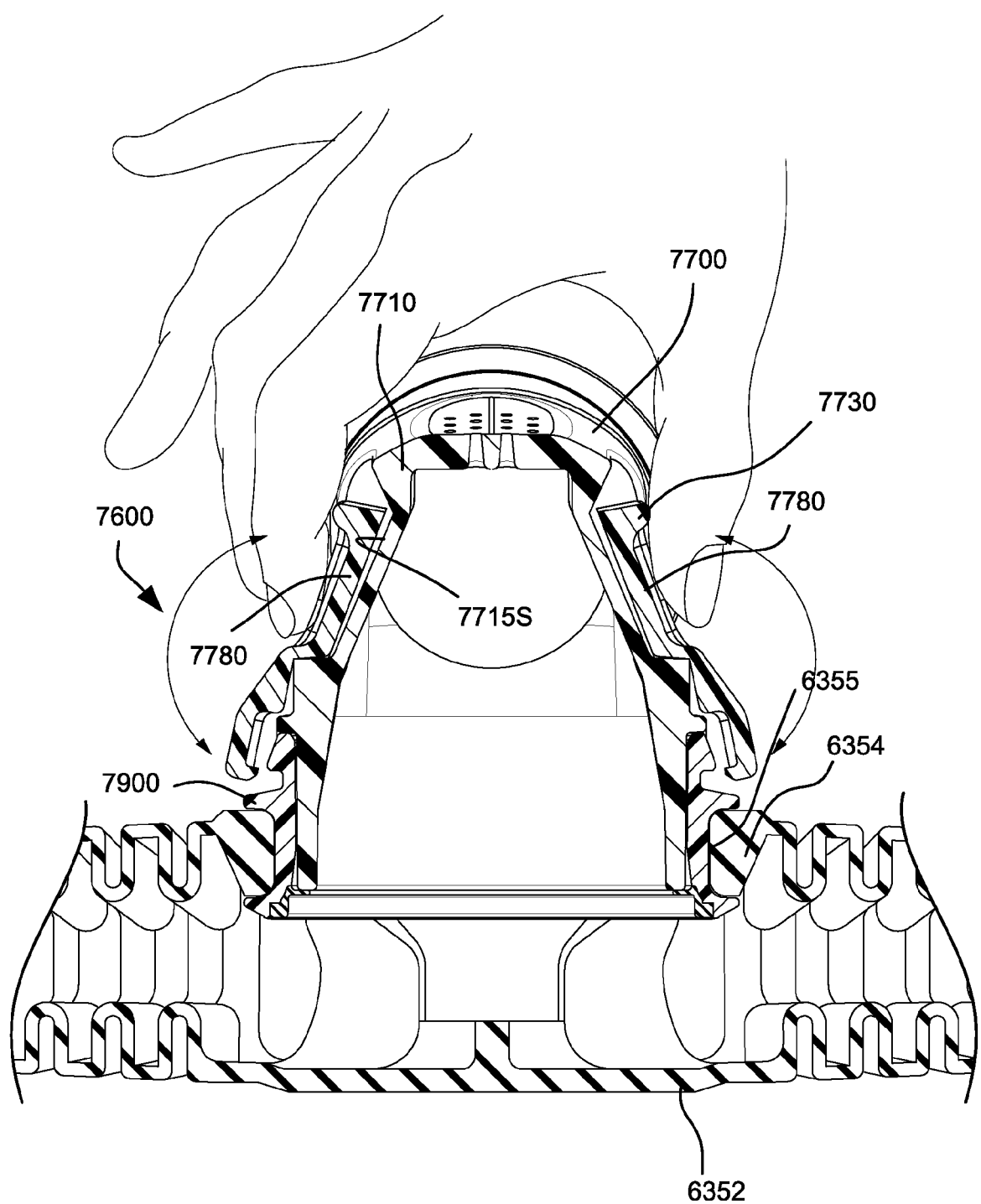

FIG. 26 is a cross-sectional view of a patient interface including a connector assembly according to an example of the present technology with the elbow assembly being manually disengaged from the ring member.

Figure 27:
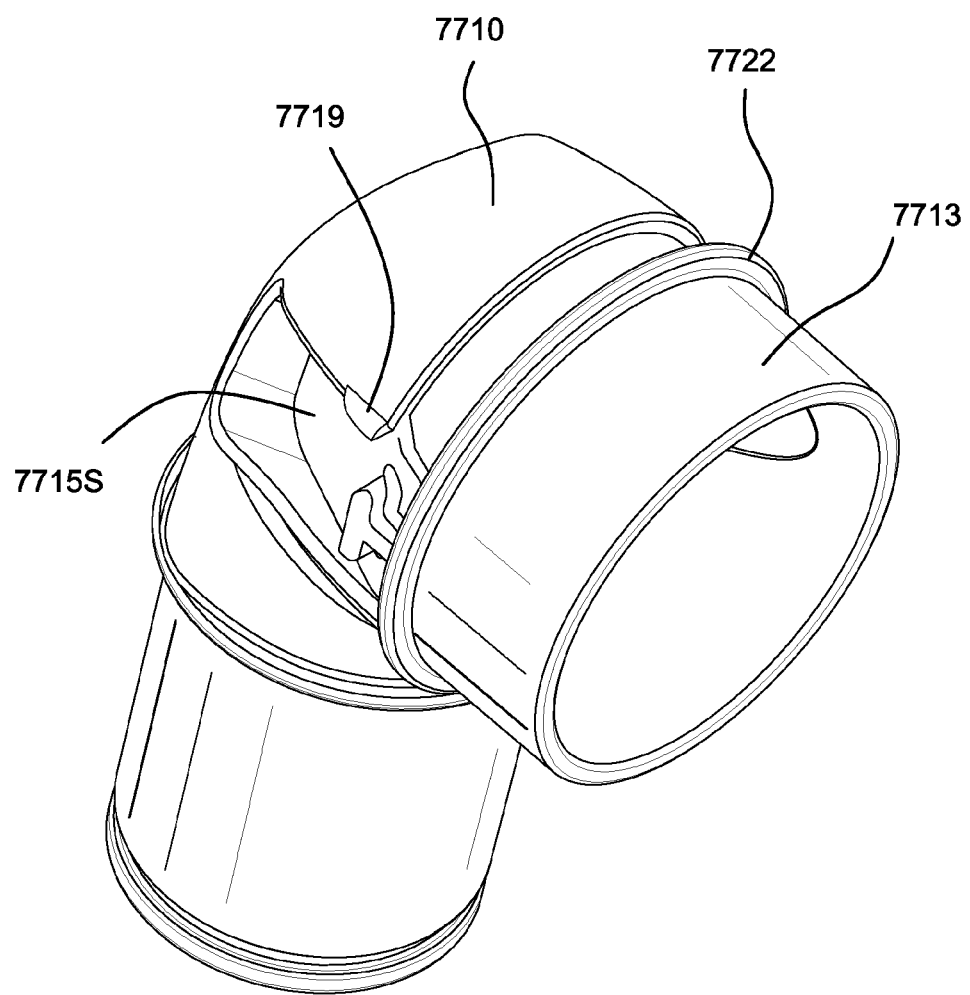

FIG. 27 is a perspective view of an elbow member according to another example of the present technology.

Figure 28:
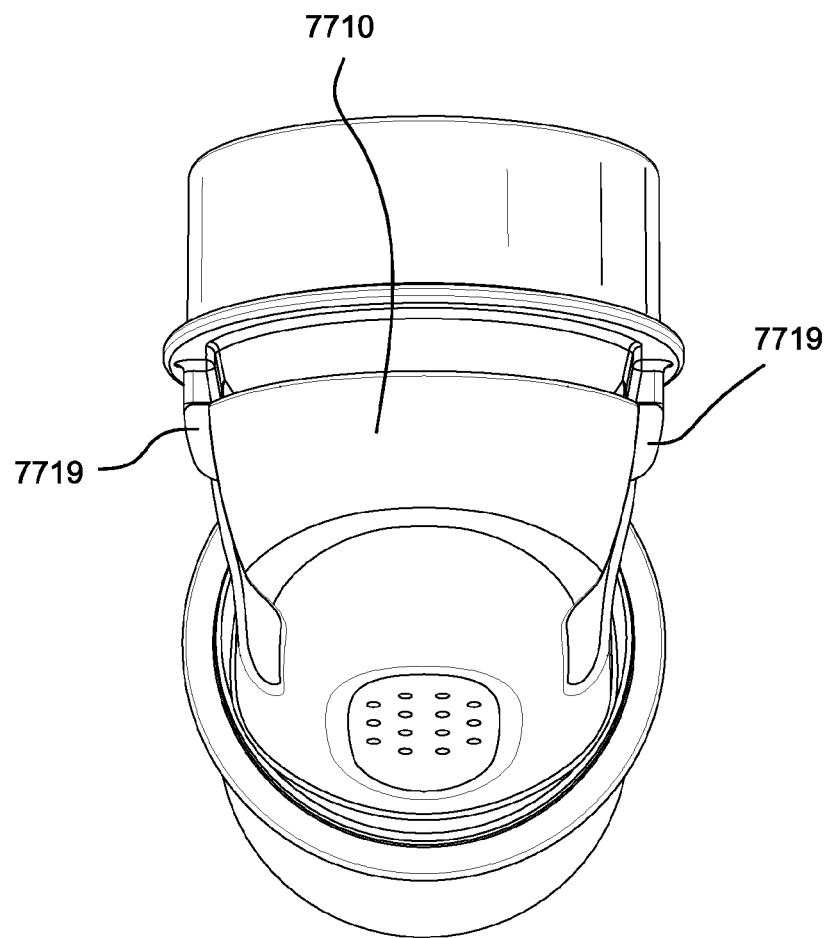

FIG. 28 is a top view of the elbow member shown in FIG. 27.

Figure 29:
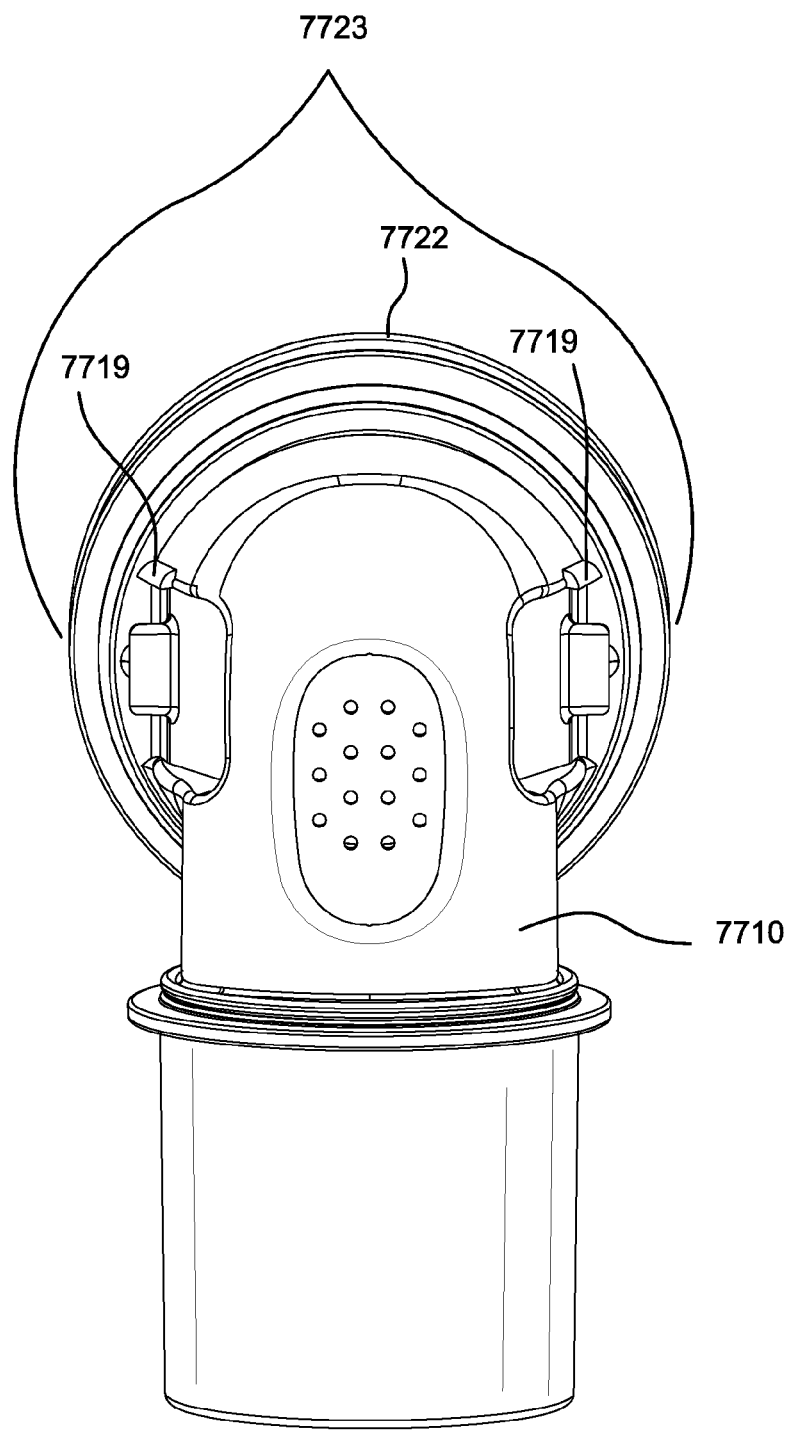

FIG. 29 is a rear view of the elbow member shown in FIG. 27.

Figure 30:
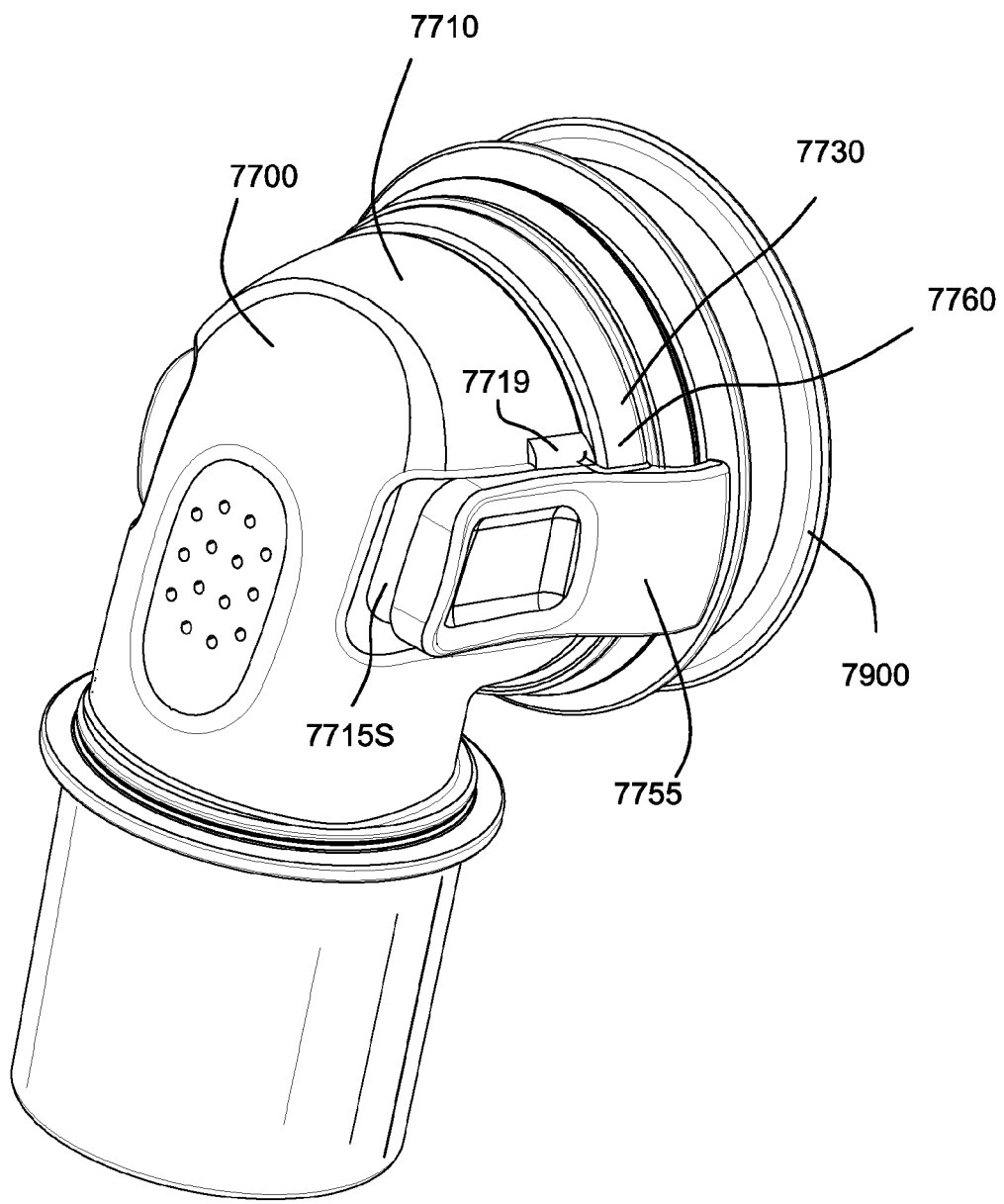

FIG. 30 is a perspective view of the elbow member shown in FIG. 27 with a clip member connected thereto.

Figure 31:
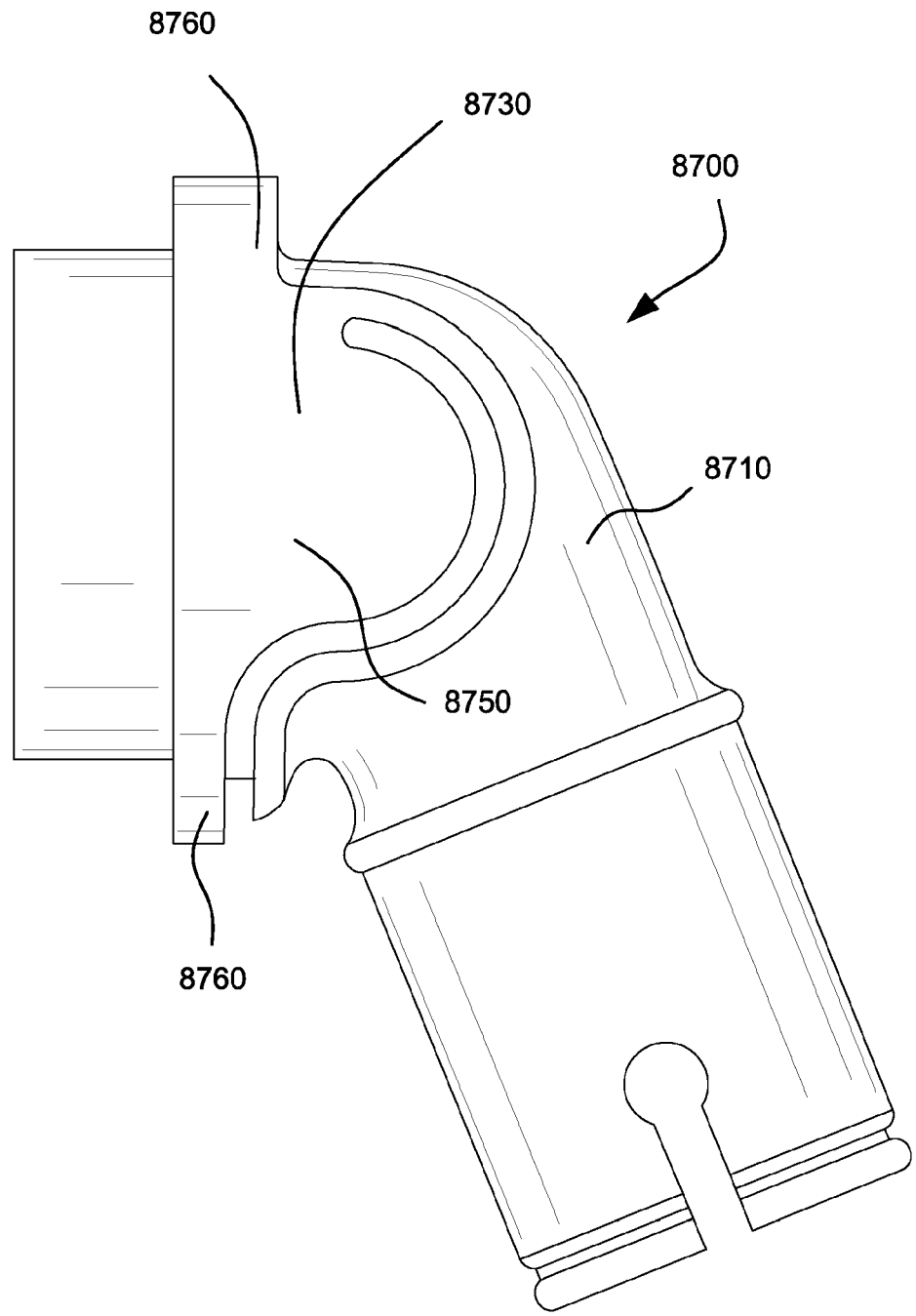

FIG. 31 is a side view of an integral elbow member and clip member according to another example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
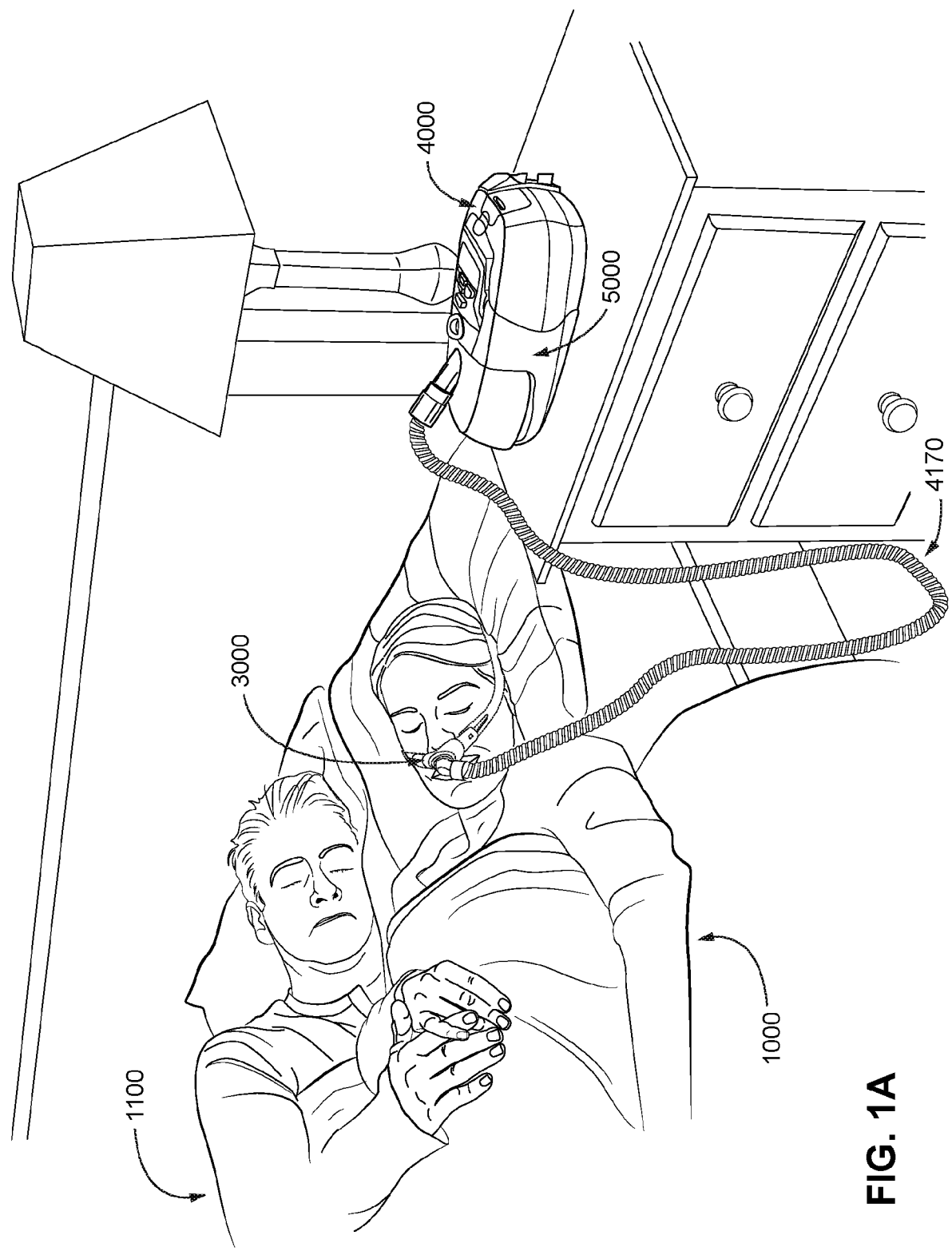
Figure 1B:
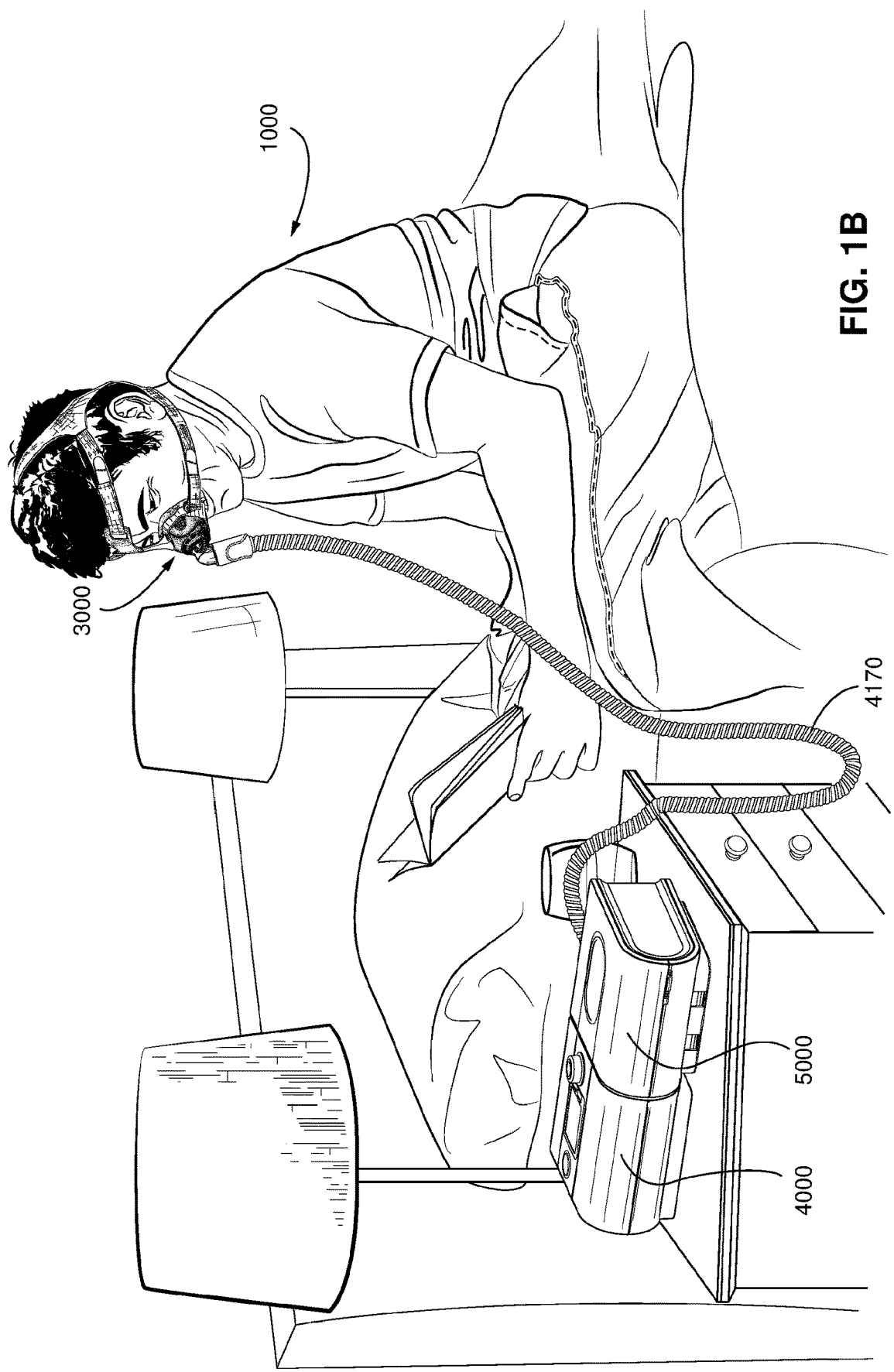
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

With reference to FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

FIG. 4 shows a non-invasive patient interface 6000 in accordance with one aspect of the present technology. As illustrated, the patient interface 6000 comprises the following functional aspects: a cushion assembly 6150, a positioning and stabilising structure 6300 and a connection port 6600 for connection to air circuit 4170. In some forms a functional aspect may be provided by one or more physical components. In some forms, one physical component may provide one or more functional aspects.

The cushion assembly 6150 comprises a seal-forming structure 6100 and a plenum chamber 6200. In use the plenum chamber 6200 receives the supply of air at positive pressure from the air circuit 4170 and the seal-forming structure 6100 is arranged to seal with an area surrounding an entrance to the airways of the patient so as to facilitate the supply of air at positive pressure to the airways.

In the form of the present technology illustrated in FIG. 4, the positioning and stabilising structure 6300 comprises two tubes 6350 (e.g., made of flexible silicone) that deliver pressurised air received from a conduit forming part of the air circuit 4170 from the RPT device to the patient's airways, for example through the plenum chamber 6200 and seal-forming structure 6100. Each tube 6350 is positioned in use on different sides of the patient's head and extending across the respective cheek region, above the respective ear (superior to the otobasion superior on the patient's head) to the connection port 6600 on top of the patient's head.

Positioning and stabilising structure 6300 may be referred to as "headgear" since it engages the patient's head in order to hold the patient interface 6000 in a sealing position. The tubes 6350 are an integral part of the headgear 6300 of patient interface 6000 to position and stabilise the seal-forming structure 6100 of the patient interface to the appropriate part of the patient's face (for example, the nose and/or mouth). This allows the conduit of air circuit 4170 providing the flow of pressurised air to connect to a connection port 6600 of the patient interface, e.g., in a position other than in front of the patient's face.

In certain forms of the present technology, the patient interface 6000 may comprise a connection port 6600 located proximal a top, side or rear portion of a patient's head. For example, in the form of the present technology illustrated in FIG. 4, the connection port 6600 is located on top of the patient's head.

In the form of the technology shown in FIG. 4, the two tubes 6350 are fluidly connected at their upper end to each other and to connection port 6600. In one embodiment, the two tubes are integrally formed while in other embodiments the tubes are separate components that are connected together in use and may be disconnected, for example for cleaning or storage.

An intermediate conduit portion or attachment region 6352 (e.g., made of flexible silicone) is provided to fluidly connect the two tubes 6350 to each other at their upper end. The intermediate conduit portion 6352 includes an opening or aperture connectable in use to the connection port 6600. The intermediate conduit portion 6352 may be integrally formed with the two tubes, or may be in the form of a separate connector comprising end portions each fluidly connectable to respective tubes 6350.

In one example, for example as shown in FIG. 4, the positioning and stabilising structure 6300 comprises a rear headgear strap 6310 connected between the two tubes 6350 positioned on each side of the patient's head and passing around the back of the patient's head, for example overlaying or lying inferior to the occipital bone of the patient's head in use.

In certain forms of the present technology, the positioning and stabilising structure 6300 comprises an adjustment mechanism 6360 configured to allow the positioning and stabilising structure 6300 to be dimensionally adjusted. For example, the patient interface 6000 shown in FIG. 4 comprises tubes 6350 comprising a concertina tube section 6362 between lengths of the tubes 6350 without concertinas.

Further examples and details of the patient interface 6000 are described in PCT Publication No. WO 2017/124155, which is incorporated herein by reference in its entirety.

It should be appreciated that aspects of the present technology may be adapted for use with other suitable interface arrangements and types, e.g., full-face/oro-nasal interface, nasal interface, nasal prongs.

Connector Assembly

FIGS. 5 to 26 show a connection port 7600 for the patient interface 6000 according to another example of the present technology. While the present technology is described with reference to patient interface 6000, it is to be understood that the technology is not limited to such particular example and may be adapted for use with other suitable interface arrangements and types.

In the illustrated example, the connection port 7600 is in the form of a connector assembly structured and arranged to provide a releasable connection between the patient interface 6000 and the air circuit 4170.

The connector assembly 7600 comprises an elbow assembly 7700 configured to connect to the air circuit 4170 (e.g., via a swivel connector 7790) and a ring member 7900 configured to connect to the patient interface 6000. As described in greater detail below, the elbow assembly 7700 is repeatedly engageable with and removably disengageable from (i.e., connectable to and disconnectable from) the ring member 7900 to facilitate a releasable or separable connection between the patient interface 6000 and the air circuit 4170.

Elbow Assembly

The elbow assembly 7700 includes an elbow member 7710 having a first end portion 7712 and a second end portion 7714. In the illustrated example, the elbow member 7710 includes a 90° bend such that the first end portion 7712 is generally perpendicular to the second end portion 7714, i.e., central axis of the first end portion 7712 is at a 90° angle to the central axis of the second end portion 7714. However, it should be appreciated that the first end portion 7712 and the second end portion 7714 may be arranged in alternative configurations, e.g., arranged at non-perpendicular angle relative to one another.

A clip member 7730 is provided to the first end portion 7712. In the illustrated example, the clip member 7730 is structured and arranged to provide a releasable connection, e.g., releasable snap-fit connection or separable snap joint assembly, with the ring member 7900. The second end portion 7714 is provided with the swivel connector 7790 (e.g., swivel connector 7790 permanently connected to the second end portion 7714) adapted to connect to the air circuit 4170.

Elbow Member

The first end portion 7712 of the elbow member 7710 includes a recess 7715 configured and arranged to receive the clip member 7730. The recess 7715 includes an upper recessed portion 7715U extending along an upper portion of the elbow member 7710. The upper recessed portion 7715U leads into side recessed portions 7715S extending along respective sides of the elbow member 7710. The depth of the recess 7715 is selected such that the clip member 7730 provides a low profile, e.g., portions of the clip member 7730 sit only slightly proud of the exterior surface surrounding the recess 7715 of the elbow member 7710.

Each of the side recessed portions 7715S includes a lug 7716 configured and arranged to interact with pinch arms 7740 of the clip member 7730 to facilitate retention of the clip member 7730 on the elbow member 7710 and operation of the pinch arms 7740.

The first end portion 7712 also includes a tubular end portion 7713 structured to extend through the ring member 7900 and into engagement with a seal member 7950 provided to the ring member 7900 so as to provide a sealed air flow path for delivery of pressurized gas through the elbow assembly 7700 to the patient interface 6000.

The second end portion 7714 is provided with the swivel connector 7790. In an example, the swivel connector 7790 may be overmolded to the tubular end portion 7717 of the second end portion 7714 (e.g., see FIG. 14). As illustrated, the tubular end portion 7717 includes a channel 7717C to receive radially inwardly extending projection 7795 provided to the swivel connector 7790 so as to axially retain the swivel connector 7790 on the second end portion 7714.

Also, a plurality of vent holes 7720 are provided along a rear wall of the elbow member 7710 (e.g., at least 10 vent holes, e.g., 10 to 20 vent holes) to permit the exit of exhaust gases from the patient interface 6000. As illustrated, the vent holes 7720 are arranged in columns, however it should be appreciated that the vent holes may be arranged in other suitable manners, e.g., concentrically arranged. In an example, each vent hole 7720 may include a contour or taper along its length, e.g., each hole converges in the direction of exhausted gas. However, each vent hole 7720 may have other suitable shapes to direct exhaust or washout gas. Further, in the illustrated example, the vent holes 7720 may be positioned on a portion of the rear wall that is generally flat or planar such that an exit end of each vent hole is provided along a generally flat or planar surface. However, it should be appreciated that the vent holes 7720 may be positioned on a portion of the elbow member 7710 having other shapes, e.g., rounded or convex.

Clip Member

The clip member 7730 includes a pair of resilient, quick release pinch arms 7740 and a connecting portion 7760 that interconnects the pinch arms 7740, i.e., pinch arm 7740 provided at each end of the connecting portion 7760.

Each of the pinch arms 7740 includes a catch portion 7750 and a button or trigger portion 7780. The pinch arms 7740 are structured and arranged to provide a releasable snap-fit connection or separable snap joint assembly with the ring member 7900, e.g., catch portions 7750 configured to deflect and snap into a recess or undercut on the ring member 7900. The button portions 7780 are structured and arranged to be manually pinched or squeezed to deflect the catch portions 7750 for separation or release of the catch portions 7750 from the ring member 7900 and hence allow separation of the elbow assembly 7700 from the ring member 7900.

Each catch portion 7750 includes a barbed end, rib, or catch 7755 structured to provide the snap joint assembly with the ring member 7900. In the illustrated example, the catch 7755 includes a lead-in angle to facilitate push-on assembly and a 90° return angle to resist or prevent pull-off disassembly, e.g., user must deflect the catch portions 7750 via the button portions 7780 to allow disassembly. Each button or trigger portion 7780 includes a finger-grip portion 7781, e.g., recessed portion adjacent a free end of the pinch arm 7740. Also, each catch portion 7750 has a recess 7757 on an inside surface to facilitate retention of the clip member 7730 on the elbow member 7710 and operation of the pinch arms 7740.

Connection Between Clip Member and Elbow Member

In the illustrated example, the clip member 7730 and the elbow member 7710 comprise separately molded components (i.e., separate and distinct structures) that are subsequently connected to one another, e.g., snap-fit connection. For example, the clip member 7730 may be comprised of a material that is more flexible than a material of the elbow member 7710, thereby allowing the clip member 7730 to flex onto and connect to the first end portion 7712 of the elbow member 7710. In an example, a retaining arrangement is provided to connect or secure the clip member to the elbow member, e.g., a snap-fit connection or snap joint assembly.

In the illustrated example, the clip member 7730 comprises an open-ended configuration with a semi-flexible and generally semi-circular connecting portion 7760 which allows the clip member 7730 to be connected to the elbow member 7710, e.g., in a manner similar to a circlip.

For example, the connecting portion 7760 of the clip member 7730 and the upper recessed portion 7715U of the elbow member 7710 may be structured and arranged to at least partly align with one another along a direction of assembly, and the connecting portion 7760 is structured and arranged to engage over and fit into the upper recessed portion 7715U, e.g., snapped or clipped into position, to positively and releasably interconnect the clip member 7730 and the elbow member 7710 in an assembled position. The connecting portion 7760, being formed in a semi-circular or arcuate shape, and with a sufficiently small cross section, is generally semi-flexible or bendable to enable the clip member 7730 to be clipped around and onto the elbow member 7710.

The connecting portion 7760 of the clip member 7730 is structured and arranged to provide one or more functions. For example, the connecting portion 7760 provides structure to attach the clip member 7730 to the elbow member 7710. The connecting portion 7760 has a shape configured to fit into the upper recessed portion 7715U of the elbow member 7710, and a structural rigidity sufficient to hold the clip member 7730 in place on the elbow member 7710. In an example, the clip member 7730 is sufficiently flexible to allow removal, e.g., the clip member may not be so rigid that the clip member cannot be removed. However, in an alternative example, the clip member 7730 may be non-removably connected to the elbow member 7710, e.g., the clip member may be so rigid that the clip member cannot be removed. In examples in which the clip member 7730 is removable, the ability of the connecting portion 7760 to bend provides the ability for the clip member 7730 to be removed. Similarly, the resistance of the connecting portion 7760 to bending provides the ability for the clip member 7730 to remain in place on the elbow member 7710.

In an example, the catch portions 7750 of the clip member 7730 may be biased inwards so that, when the clip member 7730 is connected to the elbow member 7710, the catch portions 7750 are biased inwards to grip the elbow member 7710 and provide further resistance to removal from the elbow member 7710.

The catch portions 7750 also have features which function to retain the clip member 7730 on the elbow member 7710. Specifically, each of the pinch arms 7740 are structured and arranged to fit into a respective one of the side recessed portions 7715S such that the recess 7757 on the inside surface of each catch portion 7750 is configured to receive the lug 7716 provided in the respective side recessed portion 7715S. Such coupling arrangement (e.g., snap-joint assembly) further retains the clip member 7730 on the elbow member 7710, i.e., the catch portions 7750 need to be deflected over respective lugs 7716 to separate the clip member 7730 from the elbow member 7710. The resistance of the connecting portion 7760 to bending provides resistance to this separation from occurring.

In the illustrated example, the elbow member 7710 and the clip member 7730 provide a two-part assembly or construction. An exemplary advantage of such two-part construction is that it may allow manufacture with fewer restraints on materials. For example, the clip member 7730 and the elbow member 7710 comprise separately molded components so that there is less co-dependence between the clip member 7730 and the elbow member 7710, e.g., clip member 7730 not subject to material constraints of the elbow member 7710. In an example, the clip member 7730 and the elbow member 7710 comprise different materials and/or different material properties relative to one another. In an example, the clip member 7730 and the elbow member 7710 are not molded in one piece from the same material.

In an example, the elbow member 7710 may be comprised of a material (e.g., polycarbonate) that is more rigid than a material of the clip member 7730 (e.g., nylon-12). The material (e.g., nylon-12) of the clip member 7730 may be relatively flexible and robust, e.g., facilitate flexing of the pinch arms, resistant to wear, maintain connection to elbow member. The material (e.g., polycarbonate) of the elbow member 7710 may be relatively rigid, e.g., resistant to wear, clear to facilitate cleaning, facilitate manufacturing.

Furthermore, the two-part construction may allow each part to be less complex in geometry, resulting in an assembly that may allow simpler tooling for manufacture.

In the illustrated example, the clip member 7730 is structured and arranged to provide a releasable connection, e.g., snap-fit connection, with the elbow member 7710. Such releasable or separable arrangement may be advantageous to facilitate cleaning of the clip member 7730 and the elbow member 7710 when separated.

In an alternative example, the clip member 7730 may not be removably connected to the elbow member 7710, e.g., clip member may be permanently connected to the elbow member. Such non-removable arrangement may be advantageous as it reduces the possibly of the clip member being lost or broken. Since the clip member is outside of the air flow path, a thorough cleaning may not be as essential, e.g., compared to components exposed to the air flow path.

In an example, the clip member 7730 and the elbow member 7710 may comprise separately molded components that are subsequently permanently connected to one another such that the clip member 7730 may not be separable from the elbow member 7710. Any suitable means may be employed to permanently join or connect the clip member and the elbow member.

In one example, the clip member 7730 and the elbow member 7710 may be welded or bonded to one another, e.g., ultrasonically welded to one another. For example, the clip member 7730 may be connected to the elbow member 7710 as described above, and then one or more portions (e.g., a center portion) of the connecting portion 7760 of the clip member 7730 may be welded or bonded to the elbow member 7710 to permanently secure the clip member to the elbow member. This connection would enable the connecting portion to provide the torsion (and resistance to torsion) sufficient for operation of the pinch arms 7740.

Alternatively, the elbow assembly may be structured such that the clip member can be easily assembled to the elbow member but structure of the elbow member and/or clip member makes disassembly difficult or challenging. Such elbow assembly with separately manufactured elbow member and clip member may achieve desired advantages (e.g., fewer restraints on material selection) while avoiding the additional welding or bonding operation to fix the clip member to the elbow member.

For example, as shown in FIGS. 27-30, the elbow member 7710 may include a tab or stop 7719 along an upper edge of each of the side recessed portions 7715S. Each tab 7719 projects generally laterally outwardly from the elbow member away from the bottom of the respective side recessed portion. When the clip member 7730 is connected to the elbow member 7710, the tabs or stops 7719 are arranged to make disassembly of the clip member from the elbow member more difficult. That is, the tabs or stops 7719 are arranged so that the pinch arms of the clip member have to be deflected further apart from one another in order to clear the tabs or stops 7719 for separation.

As illustrated in FIG. 30, when the clip member 7730 is connected to the elbow member 7710, the tabs 7719 project outwardly and over sides of the clip member 7730 to provide resistance to removal or "unwrapping" of the clip member 7730 from the recess 7715 of the elbow member. The tabs 7719 are located upward of the catch portions 7750 and rearward of the connecting portion 7760 of the clip member (as viewed in FIG. 30), which positioning assists in preventing the catch portions 7750 from being pushed upwards and rearwards.

The elbow assembly 7700 may also have structure to assist in preventing the catch portions 7750 from being pushed forwards to remove the clip member 7730 from the elbow member 7710. In the illustrated example, the first end portion 7712 of the elbow member 7710 comprises a radially outwardly extending ridge or flange 7722 that acts as a stop to prevent over-insertion of the elbow assembly 7700 into the ring member 7900, i.e., the flange 7722 abuts the ring member 7900 when the elbow assembly is fully inserted into the ring member 7900 (e.g., see FIG. 12). In an example, as shown in FIG. 29, a portion of this flange 7722 may be wider (i.e., the widened portion extends further radially outwardly) to form a shelf 7723, e.g., at least along the edge of the upper recessed portion 7715U of the elbow member 7710 adapted to receive the connecting portion 7760 of the clip member 7730. The shelf 7723 may function as a barrier to assist in preventing the connecting portion 7760 and hence the entire clip member 7730 from being pushed forwards out of the upper recessed portion 7715U of the elbow member 7710.

Ring Member

The ring member 7900 is configured to be removably and sealingly secured in the opening or aperture of the patient interface 6000, i.e., in the aperture 6355 of the intermediate conduit portion 6352 that interconnects the two tubes 6350 of the headgear 6300 (see FIGS. 23 to 26).

As best shown in FIG. 22, the ring member 7900 comprises a first side 7910 adapted to be located in an interior side of the intermediate conduit portion 6352 and a second side 7920 adapted to be located in an exterior side of the intermediate conduit portion 6352 when the ring member 7900 is secured in the aperture 6355. The ring member 7900 comprises a first flange 7915 on the first side 7910 and a second flange 7925 on the second side 7920. The first and second flanges 7915, 7925 define a headgear channel 7930 that sealingly engages the intermediate conduit portion 6352 of the headgear 6300 when the ring member 7900 is secured in the aperture 6355, i.e., the circumferential surface of the channel 7930 is adapted to sealing engage the lip portion 6354 that defines the aperture 6355 in the intermediate conduit portion 6352 (e.g., see FIGS. 25 and 26).

When the lip portion 6354 is engaged within the channel 7930, the ring member 7900 is secured into a substantially fixed position (i.e., headgear fits between the first and second flanges 7915, 7925 to help prevent the ring member 7900 from being separated from the headgear unintentionally) and also unable to freely rotate due to surface friction. Also, such engagement resists the flow of air through the aperture 6355 between the ring member 7900 and the intermediate conduit portion 6352. The ring member 7900 can be removed from patient interface 6000 (e.g., for cleaning, inspection), e.g., by peeling the silicone material of the intermediate conduit portion 6352 away from the ring member 7900.

The ring member 7900 also includes a clip flange 7940 configured and arranged to engage the clip member 7730 when the elbow assembly 7700 is releasably engaged with the ring member 7900. The clip flange 7940 is provided adjacent the second flange 7925, such that the clip flange 7940 and the second flange 7925 define a clip channel 7945 for matingly receiving the catches 7755 of the clip member 7730. In the illustrated example, the clip flange 7940 provides a lead-in angle, e.g., an inclined surface or ramp, in a direction of assembly to facilitate push-on assembly of the elbow assembly 7700 to the ring member 7900. The clip flange 7940 also provides a 90° return angle to resist or prevent pull-off disassembly, e.g., user must deflect the catch portions 7750 via the button portions 7780 to allow disassembly.

The ring member 7900 also includes a seal member 7950 along its inner periphery adjacent the first side 7910. The seal member 7950 is configured and arranged to provide a seal between the ring member 7900 and the elbow assembly 7700 when the elbow assembly 7700 is connected to the ring member 7900.

Releasable Connection Between Elbow Assembly and Ring Member

The elbow assembly 7700 releasably connects to the ring member 7900 via the pinch arms 7740, e.g., snap-fit or snap joint assembly. Specifically, the clip channel 7945 is structured to receive the rib or catch 7755 of each of the catch portions (e.g., rib or catch arranged to clasp, claw or hook over the clip flange to provide a secure connection) to releasably retain the elbow assembly 7700 to the ring member 7900 and form a swivel connection, i.e., allow 360° free rotation of the elbow assembly 7700 relative to the ring member 7900 about the axis of the ring member 7900. That is, the rib or catch 7755 at the free end of each catch portion 7750 is configured to engage over and behind the clip flange 7940, e.g., with a snap-fit, to releasably connect the elbow assembly 7700 to the ring member 7900 and prevent unintentional disengagement.

The inclined surface or ramp 7941 of the clip flange 7940 in a direction of assembly is configured to enable easier and smoother attachment of the elbow assembly 7700 to the ring member 7900. During attachment of the elbow assembly 7700 to the ring member 7900, the catch portions 7750 and catches 7755 thereof must be forced to deflect or pivot radially outwards to receive the clip flange 7940 as they engage over and behind the clip flange 7940, and twist each side of the connection portion 7760. Minimising this force may improve the ease of use of the elbow assembly. The inclined surface 7941 of the clip flange 7940 and the lead-in angle of the catches 7755 enables the force applied to the clip member to be applied over a greater distance, reducing the required force to spread the catch portions and improving ease of use.

The button portions 7780, at an end opposite respective catches 7755, may be manually pinched or squeezed to disengage the catches 7755 from the clip flange 7940 on the ring member 7900.

The lug 7716 within each of the side recessed portions 7715S of the elbow member 7710 provides the functions of a fulcrum and a bottoming-out stop. In the illustrated example, the lug 7716 comprises a T-shape. The cross-portion the T-shaped lug 7716 functions as a fulcrum on which the respective catch portion 7750 pivots. As noted above, each catch portion 7750 pivots during engagement in order to receive the clip flange 7940 of the ring member 7900. Additionally, each catch portion 7750 is pivoted during disengagement via the respective button portion 7780. FIG. 26 shows the catch portions pivoted to disengage the catches 7755 from the clip flange 7940 on the ring member 7900, upon the button portions 7780 being manually pinched or squeezed.

The leg portion of the T-shaped lug 7716 functions as a stop to prevent bottoming out of the respective catch portion 7750 as it pivots into its operative, connecting position, when the button portions are manually released. Alternatively, or additionally, a flange may be provided around the body of the elbow member underneath the clip member to function as a stop to limit movement of the catch portions.

Another function of the connecting portion 7760 of the clip member 7730 is to provide resistance to the catch portions 7750 pivoting. As discussed above, the catch portions 7750 pivot in order to receive and release the clip flange 7940 of the ring member 7900. However, the catch portions preferably do not pivot in the absence of pressure on the button portions by the user, otherwise the clip member would not function to secure the elbow member to the ring member. The connecting portion of the clip member connects to each catch portion substantially in line with the point about which the catch portion pivots. Pivoting of the catch portions results in torsion in the connecting portion. Thus, the connecting portion 7760 is designed with sufficient structural rigidity such that there is sufficient resistance to torsion that the catch portions do not pivot unnecessarily. However, the connecting portion must allow some amount of torsion in order to permit pivoting of the catch portions to enable the catches to receive the clip flange of the ring member and to release the clip flange from the ring member when the button portions are manually pinched or squeezed.

Seal Between Elbow Assembly and Ring Member

The ring member 7900 comprises the seal member 7950, e.g., flexible flange or radial lip seal, arranged to engage the elbow assembly 7700 to provide a seal for the air flow path when the elbow assembly 7700 is connected to the ring member 7900. In the illustrated example, the sealing mechanism is separate from the retention features, e.g., elbow member 7710 is adapted to form seal with the ring member 7900 and the clip member 7730 is adapted to releasably connect the elbow assembly to the ring member 7900.

As illustrated in FIGS. 12 and 13, the leading edge of the tubular end portion 7713 of the elbow member 7710 forms a face seal with the seal member 7950 when the elbow assembly 7700 is inserted into the ring member 7900, e.g., leading edge of the tubular end portion 7713 deforms the seal member 7950 to form a seal. This form of engagement minimises surface area contact to reduce friction, thereby allowing a seal to form between the components while allowing the elbow assembly to swivel freely relative to the ring member. As the seal member is resilient, the seal member resiliently returns to its original, cantilever position when the elbow assembly is removed from the ring member.

Also, the first end portion 7712 of the elbow member 7710 comprises the radially outwardly extending ridge 7722 that acts as a stop to prevent over-insertion of the elbow assembly 7700 into the ring member 7900.

In the illustrated example, a seal groove 7905 is provided to an inner periphery or bore of the ring member 7900 adjacent the first side, i.e., adjacent the first flange 7915 adapted to be located in an interior side of the intermediate conduit portion 6352 of the headgear 6300. The seal groove 7905 is arranged to receive the seal member 7950 and secure the seal member 7950 in an operative position (e.g., see FIG. 13).

In the illustrated example (e.g., see FIG. 13), the seal member 7950 includes a generally L-shaped connecting portion 7952 and a radial sealing portion 7954 (e.g., flexible flange or radial lip seal) projecting radially inwards from the connecting portion 7952. As illustrated, the seal groove 7905 is generally L-shaped to receive the L-shaped connecting portion 7952. In an example, the seal member 7950 may be bonded or overmolded to the ring member 7900.

In an example, as shown in FIG. 13, a tapered portion 7907 may be provided to the bore of the ring member 7900 adjacent the groove 7905, e.g., tapered portion reduces bore diameter from the seal groove to the main internal diameter of the bore. In an example, the tapered portion 7907 may be configured and arranged to allow the radial sealing portion 7954 of the seal member 7950 to project radially inwards in a cantilevered manner without minimal contact on either side of the radial sealing portion.

Decoupling Arrangement

The connector assembly 7600 provides decoupling of the air circuit 4170 from the patient interface, e.g., to enhance the decoupling of tube drag on the patient interface to prevent seal instability.

One form of decoupling is provided by the pinch arms 7740 which form the swivel connection allowing 360° free rotation of the elbow assembly 7700 relative to the ring member 7900. Another form of decoupling is provided by the swivel connector 7790 allowing 360° free rotation of the swivel connector 7790 (and the air circuit 4170 connection thereto) relative to the elbow member 7710.

The tubular end portion 7713 at the first end portion of the elbow member 7710 may be provided with a textured surface finish. Such textured surface finish may help prevent squeaking when the elbow member is rotated within the ring member in use. Additionally, the textured surface finish may reduce the torque required to rotate the elbow member within the ring member, i.e., smoothes the rotation. This arrangement reduces forces/torque applied to the headgear by the air circuit 4170 (tube drag), e.g., when the patient moves.

The outer surfaces of the ring member 7900, and in particular the outer surfaces that contact the catch portions 7750 during assembly/disassembly of the elbow assembly and the ring member, may also be provided with a textured surface finish, e.g., to reduce friction to facilitate assembly/disassembly.

Low Profile Clip Member

In the illustrated example, the clip member 7730 provides a low profile, e.g., the clip member is received in the recess of the elbow member such that one or more portions of the clip member sit only slightly proud of the exterior surface surrounding the recess of the elbow member.

For example, as shown in FIG. 9, the clip member 7730 is received in the recess 7715 of the elbow member 7710 such that the button portions 7780 sit only slightly proud of the exterior surface surrounding the recess 7715.

As explained above, the catch portions 7750 are arranged to pivot on respective lugs 7716 on the elbow member 7710. The lugs 7716 are provided within respective side recessed portions 7715S of the elbow member 7710, and therefore the overall length that the lugs extend outwardly from the elbow member (i.e., outwardly beyond the exterior surface surrounding the side recessed portions) is shorter than if the lugs were provided on an un-recessed surface of the elbow member. Additionally, each catch portion 7750 includes the recess 7757 to receive a respective lug 7716 which further reduces the outward extent of the clip member 7730 when the clip member is connected to the elbow member 7710.

In an example, to create the side recessed portions 7715S in the elbow member 7710, side walls of each side recessed portion 7715S extend inwardly from outer side walls of the elbow member 7710 defining the exterior surface, rather than cutting out material of the side walls of the elbow member (i.e., thinning out outer side wall to create recessed portions). FIG. 8 shows walls of the side recessed portions 7715S extending inward from outer side walls of the elbow member 7710 and into the flow path defined by the elbow member 7710.

In an example, the side recessed portions 7715S and the clip member 7730 are configured and arranged such that the outside surfaces of the button portions 7780 are not completely flush with the exterior surface of the elbow member 7710, e.g., to provide button portions 7780 that protrude slightly to facilitate use by the patient (e.g., as shown in FIG. 9).

In an example, the low-profile button portions 7780 are less likely to catch the patient's hair and get tangled in use. The connecting portion 7760 of the clip member 7730 is also recessed within the upper recessed portion 7715U (e.g., see FIG. 11), and therefore less likely to get tangled up in the patient's hair in use.

In an example, as shown in FIG. 26, the side recessed portions 7715S may also function as "stops" to prevent excessive inwards movement or deflection of the button portions 7780 in use, e.g., to enhance durability.

Alternative Examples

It should be appreciated that aspects of the present technology may be adapted for use with other suitable connector arrangements.

For example, the connector assembly may not comprise an elbow at the air circuit connection to the patient interface. In an alternative example, aspects of the clip member may be applied to other connector arrangements, e.g., aspects of the clip member may be applied to an end of the air circuit (either short or long tube) in which the air circuit is coaxial with the connector.

In alternative examples, the connector assembly may be adapted for use with other suitable interface arrangements, e.g., full-face mask system, nasal mask system. In the case of a full-face mask system, the connector assembly may comprise an AAV.

In the illustrated example, the elbow assembly comprises vent holes. In an alternative example, the elbow assembly may not comprise vent holes if vents are provided elsewhere in the system.

In an alternative example, the clip member and the elbow member may be integrally formed as a one-piece construction. For example, FIG. 31 shows an example of an elbow assembly 8700 including an integral clip member 8730 and elbow member 8710. In such example, the catches of the clip member 8730 may be provided to respective catch portions 8750 as described above and/or one or more catches may be provided to connecting portions 8760 connecting the catch portions.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Glossary

For the purposes of the present technology disclosure, in certain forms of the present technology, one or more of the following definitions may apply. In other forms of the present technology, alternative definitions may apply.

5.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.4.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.4.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.4.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.4.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.4.4 Anatomy
5.4.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.4.4.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.4.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.4.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space:

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.4.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.4.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.4.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.4.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.4.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.5 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.6 REFERENCE SIGNS LIST

| Feature Item | Number |
| --- | --- |
| patient | 1000 |
| bed partner | 1100 |
| patient interface | 3000 |
| non - invasive patient interface | 3000 |
| seal - forming structure | 3100 |
| plenum chamber | 3200 |
| positioning and stabilising structure | 3300 |
| vent | 3400 |
| connection port | 3600 |
| forehead support | 3700 |
| RPT device | 4000 |
| air circuit | 4170 |
| humidifier | 5000 |
| patient interface | 6000 |
| seal - forming structure | 6100 |
| cushion assembly | 6150 |
| plenum chamber | 6200 |
| headgear | 6300 |
| rear headgear strap | 6310 |
| tube | 6350 |
| intermediate conduit portion | 6352 |
| lip portion | 6354 |
| aperture | 6355 |
| adjustment mechanism | 6360 |
| concertina tube section | 6362 |
| connection port | 6600 |
| connector assembly | 7600 |
| elbow assembly | 7700 |
| elbow member | 7710 |
| first end portion | 7712 |
| tubular end portion | 7713 |
| second end portion | 7714 |
| recess | 7715 |
| side recessed portion | 7715S |
| upper recessed portion | 7715U |
| lug | 7716 |
| tubular end portion | 7717 |
| channel | 7717C |
| stop | 7719 |
| vent hole | 7720 |
| ridge | 7722 |

5.6 REFERENCE SIGNS LIST

| Feature Item | Number |
|---|---|
| flange | 7722 |
| shelf | 7723 |
| clip member | 7730 |
| pinch arm | 7740 |
| pinch arm | 7740 |
| catch portion | 7750 |
| catch portion | 7750 |
| catch | 7755 |
| recess | 7757 |
| connection portion | 7760 |
| button portion | 7780 |
| finger - grip portion | 7781 |
| swivel connector | 7790 |
| projection | 7795 |
| ring member | 7900 |
| seal groove | 7905 |
| tapered portion | 7907 |
| first side | 7910 |
| first flange | 7915 |
| second side | 7920 |
| second flange | 7925 |
| channel | 7930 |
| clip flange | 7940 |
| ramp | 7941 |
| clip channel | 7945 |
| seal member | 7950 |
| connecting portion | 7952 |
| sealing portion | 7954 |
| elbow assembly | 8700 |
| elbow member | 8710 |
| clip member | 8730 |
| connecting portion | 8760 |

The invention claimed is:

1. A patient interface to deliver a flow of air at a positive pressure with respect to ambient air pressure to an entrance to the patient's airways including at least the entrance of a patient's nares while the patient is sleeping, to ameliorate sleep disordered breathing, the patient interface comprising:
a seal-forming structure configured to form a seal with a region of a patient's face surrounding the entrance to the patient's airways;
a positioning and stabilising structure configured to provide a force to hold the seal-forming structure in a therapeutically effective position on a patient's head; and
a connector assembly configured to connect to an air circuit, the connector assembly comprising:
a ring member configured to be removably and releasably secured in an aperture of an attachment region of the patient interface; and
an elbow assembly configured to connect to the air circuit, the elbow assembly repeatedly connectable to and disconnectable from the ring member,
the elbow assembly including an elbow member and a clip member, the clip member comprising a separate and distinct structure from the elbow member,
wherein the elbow member and the clip member are separable, and comprise separately molded components that are subsequently connected to one another,
wherein the elbow member includes an exterior surface arranged outside an air flow path formed by the elbow member,
wherein the exterior surface of the elbow member includes a recess configured and arranged to receive at a least a portion of the clip member, and
wherein the clip member is configured and arranged to releasably connect the elbow assembly to the ring member, and the elbow member is configured and arranged to form a seal with the ring member when the elbow assembly and the ring member are connected to one another.

2. The patient interface according to claim 1, wherein the clip member is configured and arranged to provide a separable snap joint assembly with the ring member.

3. The patient interface according to claim 1, wherein the elbow member includes a 90° bend.

4. The patient interface according to claim 1, further comprising a swivel connector provided to the elbow member, the swivel connector configured to connect to the air circuit.

5. The patient interface according to claim I, wherein the clip member includes a pair of resilient, quick release pinch arms and a connecting portion that interconnects the pinch arms.

6. The patient interface according to claim 5, wherein each of the pinch arms includes a catch portion and a button portion, each catch portion including a catch configured to provide a snap joint assembly with the ring member.

7. The patient interface according to claim 5, wherein the recess of the elbow member includes an upper recessed portion configured to receive the connecting portion and side recessed portions configured to receive respective pinch arms.

8. The patient interface according to claim 7, wherein each of the side recessed portions includes a lug configured and arranged to interact with a respective one of the pinch arms to facilitate retention of the clip member on the elbow member and operation of the pinch arms.

9. The patient interface according to claim 1, wherein the ring member includes a seal member, and the elbow member includes a tubular end portion configured to extend through the ring member and into engagement with the seal member to provide a sealed air flow path for delivery of pressurized gas through the elbow assembly to the patient interface.

10. The patient interface according to claim 1, wherein the elbow member includes a plurality of vent holes to permit the exit of exhaust gases from the patient interface.

11. The patient interface according to claim 1, wherein the elbow member is comprised of a material that is more rigid than a material of the clip member.

12. The patient interface according to claim 1, wherein the ring member comprises a first flange and a second flange forming a channel that sealingly engages the attachment region of the patient interface.

13. The patient interface according to claim 1, wherein the ring member comprises a clip flange configured and arranged to engage the clip member when the elbow assembly is releasably connected to the ring member.

14. The patient interface according to claim 13, wherein the clip flange forms a clip channel configured and arranged to matingly receive catches of the clip member.

15. The patient interface according to claim 13, wherein the clip flange provides an inclined surface in a direction of assembly to facilitate push-on assembly of the elbow assembly to the ring member.

16. The patient interface according to claim 1, wherein the elbow assembly and the ring member form a swivel connection allowing 360° free rotation of the elbow assembly relative to the ring member.

17. The patient interface according to claim 1, wherein the positioning and stabilising structure comprises two tubes.

18. The patient interface according to claim 17, wherein the attachment region is configured and arranged to fluidly connect the two tubes.

19. The patient interface according to claim 1, further comprising a retaining arrangement configured to connect the clip member to the elbow member.

20. The patient interface according claim 19, wherein the retaining arrangement comprises a snap joint assembly.

21. A CPAP system used for treatment of sleep disordered breathing, the CPAP system comprising:
   a CPAP device configured to supply a flow of air at a positive pressure;
   the patient interface according to claim 1;
   and an air circuit connected between the CPAP device and the patient interface to deliver the flow of air at the positive pressure from the CPAP device to the patient interface.

* * * * *